(12) United States Patent
Cameron et al.

(10) Patent No.: US 6,642,266 B2
(45) Date of Patent: Nov. 4, 2003

(54) EP4 RECEPTOR SELECTIVE AGONISTS IN THE TREATMENT OF OSTEOPOROSIS

(75) Inventors: Kimberly O. Cameron, East Lyme, CT (US); HuaZhu Ke, Ledyard, CT (US); Bruce A. Lefker, Gales Ferry, CT (US); David D. Thompson, Gales Ferry, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/991,585

(22) Filed: Nov. 16, 2001

(65) Prior Publication Data

US 2002/0040149 A1 Apr. 4, 2002

Related U.S. Application Data

(62) Division of application No. 09/738,670, filed on Dec. 15, 2000.
(60) Provisional application No. 60/171,353, filed on Dec. 22, 1999.

(51) Int. Cl.[7] .......................................... A61K 31/4015
(52) U.S. Cl. ........................ 514/424; 514/381; 548/551
(58) Field of Search ................................ 548/551, 253; 514/424, 381

(56) References Cited

U.S. PATENT DOCUMENTS

| | | | |
|---|---|---|---|
| 3,528,961 A | 9/1970 | Miles et al. | 260/162 |
| 3,780,095 A | 12/1973 | Klemm et al. | 260/518 |
| 3,987,091 A | 10/1976 | Cragoe, Jr. et al. | 260/490 |
| 3,991,106 A | 11/1976 | Cragoe, Jr. et al. | 260/519 |
| 4,033,996 A | 7/1977 | Cragoe, Jr. et al. | 260/490 |
| 4,055,596 A | 10/1977 | Cragoe, Jr. et al. | 260/534 |
| 4,113,873 A | 9/1978 | Himizu et al. | 424/274 |
| 4,115,401 A | 9/1978 | Nanthavong et al. | 260/326.43 |
| 4,175,203 A | 11/1979 | Cragoe, Jr. et al. | 560/55 |
| 4,177,346 A | 12/1979 | Nelson | 542/427 |
| 4,243,678 A | 1/1981 | Krastinat | 424/319 |
| 4,386,031 A | 5/1983 | Hilboll et al. | 260/404 |
| 4,443,477 A | 4/1984 | Witte et al. | 424/319 |
| 4,761,430 A | 8/1988 | Choay et al. | 514/562 |

FOREIGN PATENT DOCUMENTS

| | | | |
|---|---|---|---|
| DE | 2528664 | 1/1977 | ......... C07D/207/26 |
| EP | 0605193 | 7/1994 | ......... A61K/31/40 |
| FR | 0897566 | 3/1945 | |
| GB | 1478281 | 9/1911 | ........... C07C/59/00 |
| GB | 1479156 | 7/1977 | ........... C07C/59/00 |
| GB | 1553595 | 10/1979 | ......... C07D/207/12 |
| GB | 1583163 | 1/1981 | ......... C07D/207/27 |
| GB | 2330307 | 4/1999 | ......... A61K/31/557 |
| WO | WO 0021532 | 4/2000 | ......... A61K/31/41 |
| WO | WO 0021542 | 4/2000 | ......... A61K/31/66 |

OTHER PUBLICATIONS

J. Org. Chem. 26, 1961, p. 1437.
Bolander et al. 38th Annual Meeting Orthopedic Research Society, 1992.
Ke et al. Bone, 23:249–255, 1998.
Jee, W.S.S. and Ma, Y.F., Bone, 21:297–304, 1997.

*Primary Examiner*—Robert Gerstl
(74) *Attorney, Agent, or Firm*—Peter C. Richardson; Gregg C. Benson; John A. Wichtowski

(57) ABSTRACT

This invention is directed to methods of treating conditions which present with low bone mass, particularly osteoporosis, frailty, an osteoporotic fracture, a bone defect, childhood idiopathic bone loss, alveolar bone loss, mandibular bone loss, bone fracture, osteotomy, bone loss associated with periodontitis, or prosthetic ingrowth comprising administering prostaglandin agonists which are EP4 receptor selective prostaglandin agonists. This invention is especially directed to those methods wherein the EP4 receptor selective agonist is a compound of Formula I:

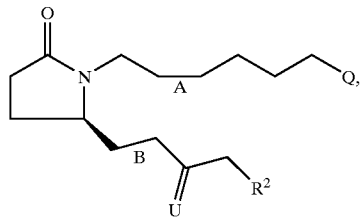

I wherein the variables are as defined in the specification.

15 Claims, No Drawings

EP4 RECEPTOR SELECTIVE AGONISTS IN THE TREATMENT OF OSTEOPOROSIS

CROSS-REFERENCE TO RELATED APPLICATIONS

This is a division of copending U.S. Ser. No. 09/738,670, filed Dec. 15, 2000, which claims priority to U.S. Provisional Application No. 60/171,353 filed Dec. 22, 1999.

BACKGROUND OF INVENTION

This invention relates to methods and pharmaceutical compositions comprising prostaglandin agonists which are useful to prevent bone loss, restore or augment bone mass and to enhance bone healing including the treatment of conditions which present with low bone mass and/or bone defects in vertebrates, and particularly mammals, including humans. This invention specifically relates to methods and pharmaceutical compositions comprising EP4 receptor selective prostaglandin agonists.

Osteoporosis is a systemic skeletal disease, characterized by low bone mass and deterioration of bone tissue, with a consequent increase in bone fragility and susceptibility to fracture. In the U.S., the condition affects more than 25 million people and causes more than 1.3 million fractures each year, including 500,000 spine, 250,000 hip and 240,000 wrist fractures annually. Hip fractures are the most serious consequence of osteoporosis, with 5–20% of patients dying within one year, and over 50% of survivors being incapacitated.

The elderly are at greatest risk of osteoporosis, and the problem is therefore predicted to increase significantly with the aging of the population. Worldwide fracture incidence is forecasted to increase three-old over the next 60 years, and one study has estimated that there will be 4.5 million hip fractures worldwide in 2050.

Women are at greater risk of osteoporosis than men. Women experience a sharp acceleration of bone loss during the five years following menopause. Other factors that increase the risk include smoking, alcohol abuse, a sedentary lifestyle and low calcium intake.

There are currently two main types of pharmaceutical therapy for the treatment of osteoporosis. The first is the use of anti-resorptive compounds to reduce the resorption of bone tissue.

Estrogen is an example of an anti-resorptive agent. It is known that estrogen reduces fractures. In addition, Black, et al. in EP 0605193A1 report that estrogen, particularly when taken orally, lowers plasma levels of LDL and raises those of the beneficial high density lipoproteins (HDL's). However, estrogen fails to restore bone back to young adult levels in the established osteoporotic skeleton. Furthermore long-term estrogen therapy has been implicated in a variety of disorders, including an increase in the risk of uterine cancer, endometrial cancer and possibly breast cancer, causing many women to avoid this treatment. The significant undesirable effects associated with estrogen therapy support the need to develop alternative therapies for osteoporosis that have the desirable effect on serum LDL but do not cause undesirable effects.

A second type of pharmaceutical therapy for the treatment of osteoporosis is the use of anabolic agents to promote bone formation and increase bone mass. This class of agents is expected to restore bone to the established osteoporotic skeleton.

Certain prostagladin agonists are disclosed in GB 1478281, GB1479156 and U.S. Pat. Nos. 4,175,203, 4,055, 596, 4,175,203, 3,987,091 and 3,991,106 as being useful as, for example, renal vasodilators.

U.S. Pat. No. 4,033,996 discloses certain 8-aza-9-oxo(and dioxo)-thia-11,12-secoprostaglandins which are useful as renal vasodilators, for the prevention of thrombus formation, to induce growth hormone release, and as regulators of the immune response.

French patent no. 897,566 discloses certain amino acid derivatives for the treatment of neurological, mental or cardiovascular disease.

J. Org. Chem. 26; 1961; 1437 discloses N-acetyl-N-benzyl-p-aminophenylmercaptoacetic acid.

U.S. Pat. No. 4,761,430 discloses certain arylbenzene-sulfonamide compounds as lipid-lowering agents.

U.S. Pat. No. 4,443,477 discloses certain sulphonamidophenylcarboxylic acids as lipid lowering agents.

U.S. Pat. No. 3,528,961 discloses certain $\epsilon$-caprolactam derivatives as dyes.

U.S. Pat. No. 3,780,095 discloses certain acylated anilinocarboxylic acids as choleretics.

U.S. Pat. No. 4,243,678 discloses certain acylhydrocarbylaminoalkanoic acids as having utility in the treatment of gastric ulcers, as sebaceous gland excretion inhibitors and for combatting skin inflammation.

U.S. Pat. No. 4,386,031 discloses certain N-benzoyl-$\omega$-anilinoalkanecarboxylic acids as antiallergic agents, thrombotic aggregation inhibitors, antiinflammatory agents and lipid-lowering agents.

In addition to osteoporosis, approximately, 20–25 million women and an increasing number of men have detectable vertebral fractures as a consequence of reduced bone mass, with an additional 250,000 hip fractures reported yearly in America alone. The latter case is associated with a 12% mortality rate within the first two years and with a 30% rate of patients requiring nursing home care after the fracture. While this is already significant, the economic and medical consequences of convalescence due to slow or imperfect healing of these bone fractures is expected to increase, due to the aging of the general population.

Estrogens have been shown (Bolander et al., 38th Annual Meeting Orthopedic Research Society, 1992) to improve the quality of the healing of appendicular fractures. Therefore, estrogen replacement therapy should be effective as a method for the treatment of fracture repair. However, patient compliance with estrogen therapy is relatively poor due to its side effects, including the resumption of menses, mastodynia, an increased risk of uterine cancer, an increased perceived risk of breast cancer, and the concomitant use of progestins. In addition, men are likely to object to the use of estrogen treatment. The need exists for a therapy which would be beneficial to patients who have suffered debilitating bone fractures and which would increase patient compliance.

It has been demonstrated that prostaglandin E2 (PGE2) can restore lost bone in an ovariectomized (OVX) rat model, a model for postmenopausal osteoporosis. Ke, H. Z., et al., Bone, 23:249–255, 1998. However there are severe side effects associated with PGE2. Jee, W. S. S. and Ma, Y. F., Bone, 21:297–304, 1997.

Although there are a variety of osteoporosis therapies, there is a continuing need and a continuing search in this field of art for alternative osteoporosis therapies. In addition, there is a need for bone fracture healing therapies. Also, there is a need for therapy which can promote bone re-growth into skeletal areas where defects exist such as defects caused or produced by, for example, tumors in bone. Further, there is a need for therapy which can promote bone re-growth into skeletal areas where bone grafts are indicated.

SUMMARY OF THE INVENTION

This invention is directed to methods of treating a condition which presents with low bone mass in a mammal comprising administering to said mammal an EP4 receptor selective agonist, a prodrug thereof or a pharmaceutically acceptable salt of said EP4 receptor selective agonist or of said prodrug.

This invention is particularly directed to such methods wherein said condition is osteoporosis, frailty, an osteoporotic fracture, a bone defect, childhood idiopathic bone loss, alveolar bone loss, mandibular bone loss, bone fracture, osteotomy, bone loss associated with periodontitis, or prosthetic ingrowth. In preferred methods of this invention, the EP4 receptor selective agonist is administered systemically, e.g., orally, subcutaneously, intramuscularly or via aerosol. In other preferred methods of this invention, the EP4 agonist is administered locally.

The methods of this invention are especially useful wherein said condition is frailty.

The methods of this invention are also especially useful wherein said condition is osteoporosis.

The methods of this invention are also especially useful wherein said condition is bone fracture or osteoporotic fracture.

Preferred EP4 selective agonists for use in the methods of this invention include compounds of Formula I:

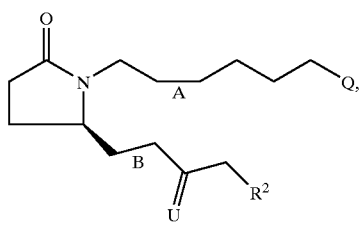

prodrugs thereof and pharmaceutically acceptable salts of said compounds or said prodrugs, wherein:

Q is $COOR^3$, $CONHR^4$ or tetrazol-5-yl;

A is a single or cis double bond;

B is a single or trans double bond;

U is

$R^2$ is α-thienyl, phenyl, phenoxy, monosubstituted phenyl and monosubstituted phenoxy, said substituents being chloro, fluoro, phenyl, methoxy, trifluoromethyl or $(C_1-C_3)$alkyl;

$R^3$ is hydrogen, $(C_1-C_5)$alkyl, phenyl or p-biphenyl;

$R^4$ is $COR^5$ or $SO_2R^5$; and $R^5$ is phenyl or $(C_1-C_5)$alkyl.

A preferred group of EP4 receptor selective agonists of Formula I for use in the methods of this invention are those compounds of Formula I wherein Q is 5-tetrazolyl and U is

forming compounds having the formula $I^A$,

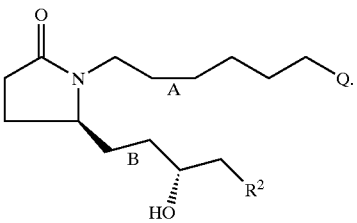

Particularly preferred compounds within this group include 5S-(4-(3-chloro-phenyl)-3R-hydroxy-butyl)-1-(6-(2H-tetrazol-5-yl)-hexyl-pyrrolidin-2-one; 5S-(3R-hydroxy-4-(3-trifluoromethyl-phenyl)-butyl)-1-(6-(2H-tetrazol-5-yl)-hexyl)-pyrrolidin-2-one; 5R-(3S-hydroxy-4-phenyl-but-1-enyl)-1-[6-(1H-tetrazol-5-yl)-hexyl]-pyrrolidin-2-one; and 5S-(3R-hydroxy-4-phenyl-butyl)-1-[6-(1H-tetrazol-5-yl)-hexyl]-pyrrolidin-2-one.

Another preferred group of EP4 receptor selective agonists of Formula I for use in the methods of this invention are those compound of Formula I wherein Q is COOH. Particularly preferred compounds within this group include 7-{2S-[3R-hydroxy-4-(3-phenoxy-phenyl)-butyl]-5-oxo-pyrrolidin-1-yl}-heptanoic acid; 7-(2S-(3R-hydroxy-4-(3-trifluoromethyl-phenyl)-butyl)-5-oxo-pyrrolidin-1-yl)-heptanoic acid; 7-{2S-[4-(3-chloro-phenyl)-3R-hydroxy-butyl]-5-oxo-pyrrolidin-1-yl}-heptanoic acid; 7-(2S-(3R-hydroxy-4-phenyl-butyl)-5-oxo-pyrrolidin-1-yl)-heptanoic acid; and 7-[2R-(3S-hydroxy-4-phenyl-but-1-enyl)-5-oxo-pyrrolidin-1-yl]-heptanoic acid.

Preferably post-menopausal women and men over the age of 60 are treated. Also preferred are individuals regardless of age who have significantly reduced bone mass, i.e., greater than or equal to 1.5 standard deviations below young normal levels.

In the methods of this invention, conditions which present with low bone mass include such conditions as, for example, osteoporosis, childhood idiopathic bone loss, alveolar bone loss, mandibular bone loss, bone fracture, osteotomy, bone loss associated with periodontitis and prosthetic ingrowth.

Methods for treating "secondary osteoporosis" are also included within the methods of this invention. "Secondary osteoporosis" includes glucocorticoid-induced osteoporosis, hyperthyroidism-induced osteoporosis, immobilization-induced osteoporosis, heparin-induced osteoporosis and immunosuppressive-induced osteoporosis in a vertebrate, e.g., a mammal (including a human being). These methods are carried out by administering to said vertebrate, e.g., mammal, a "secondary osteoporosis" treating amount of an EP4 receptor selective prostaglandin agonist, a prodrug thereof or a pharmaceutically acceptable salt of said EP4 receptor selective prostaglandin agonist or of said prodrug.

Yet another aspect of this invention is directed to methods for strengthening a bone graft, inducing vertebral synostosis, enhancing long bone extension, enhancing bone healing following facial reconstruction, maxillary reconstruction and/or mandibular reconstruction in a vertebrate, e.g., a mammal (including a human being), comprising administering to said vertebrate, e.g., a mammal which has undergone facial reconstruction, maxillary reconstruction or mandibular reconstruction, a bone enhancing amount of an EP4 receptor selective prostaglandin agonist, a prodrug thereof or a pharmaceutically acceptable salt of said EP4 receptor selective prostaglandin agonist or of said prodrug. The active EP4 receptor selective prostaglandin agonists of this invention may be applied locally to the site of bone reconstruction or may be administered systemically.

A preferred dosage is about 0.001 to about 100 mg/kg/day of an EP4 receptor selective agonits, a prodrug thereof or a pharmaceutically acceptable salt of said compound or said prodrug. An especially preferred dosage is about 0.01 to about 10 mg/kg/day of an EP4 receptor selective agonist, a prodrug thereof or a pharmaceutically acceptable salt of said compound or said prodrug.

The phrase "condition(s) which presents with low bone mass" refers to a condition where the level of bone mass is below the age specific normal as defined in standards by the World Health Organization"Assessment of Fracture Risk and its Application to Screening for Postmenopausal Osteoporosis (1994). Report of a World Health Organization Study Group. World Health Organization Technical Series 843". Included in "condition(s) which presents with low bone mass" are primary and secondary osteoporosis, as described above. Also included is periodontal disease, alveolar bone loss, post-osteotomy and childhood idiopathic bone loss. The phrase "condition(s) which presents with low bone mass" also includes long term complications of osteoporosis such as curvature of the spine, loss of height and prosthetic surgery.

The phrase "condition(s) which presents with low bone mass" also refers to a vertebrate, e.g., a mammal known to have a significantly higher than average chance of developing such diseases as are described above including osteoporosis (e.g., post-menopausal women, men over the age of 50). Other bone mass augmenting or enhancing uses include bone restoration, increasing the bone fracture healing rate, replacing bone graft surgery entirely, enhancing the rate of successful bone grafts, bone healing following facial reconstruction or maxillary reconstruction or mandibular reconstruction, prosthetic ingrowth, vertebral synostosis or long bone extension.

The methods of this invention may also be used in conjunction with orthopedic devices such as spinal fusion cages, spinal fusion hardware, internal and external bone fixation devices, screws and pins.

Those skilled in the art will recognize that the term bone mass actually refers to bone mass per unit area which is sometimes (although not strictly correctly) referred to as bone mineral density.

The term "treating", "treat" or "treatment" as used herein includes preventative (e.g., prophylactic), palliative and curative treatment.

By "pharmaceutically acceptable" it is meant the carrier, vehicle, diluent, excipients, and/or salt must be compatible with the other ingredients of the formulation, and not deleterious to the recipient thereof.

The expression "prodrug" refers to compounds that are drug precursors which, following administration, release the drug in vivo via some chemical or physiological process (e.g., a prodrug on being brought to the physiological pH or through enzyme action is converted to the desired drug form). Exemplary prodrugs upon cleavage release the corresponding drug compound.

The expression "pharmaceutically acceptable salt" refers to nontoxic anionic salts containing anions such as (but not limited to) chloride, bromide, iodide, sulfate, bisulfate, phosphate, acetate, maleate, fumarate, oxalate, lactate, tartrate, citrate, gluconate, methanesulfonate and 4-toluenesulfonate. The expression also refers to nontoxic cationic salts such as (but not limited to) sodium, potassium, calcium, magnesium, ammonium or protonated benzathine (N,N'-dibenzylethylenediamine), choline, ethanolamine, diethanolamine, ethylenediamine, meglamine (N-methylglucamine), benethamine (N-benzylphenethylamine), piperazine or tromethamine (2-amino-2-hydroxymethyl-1,3-propanediol).

The methods of this invention result in bone formation resulting in decreased fracture rates. This invention makes a significant contribution to the art by providing methods that increase bone formation resulting in prevention, retardation, and/or regression of osteoporosis and related bone disorders.

This invention is also directed to compounds selected from 7-{2S-[3R-hydroxy-4-(3-phenoxy-phenyl)-butyl]-5-oxo-pyrrolidin-1-yl}-heptanoic acid; 5S-(4-(3-chloro-phenyl)-3R-hydroxy-butyl)-1-(6-(2H-tetrazol-5-yl)-hexyl-pyrrolidin-2-one; 7-(2S-(3R-hydroxy-4-(3-trifluoromethyl-phenyl)-butyl)-5-oxo-pyrrolidin-1-yl)-heptanoic acid; 7-{2S-[4-(3-chloro-phenyl)-3R-hydroxy-butyl]-5-oxo-pyrrolidin-1-yl}-heptanoic acid; and 5S-(3R-hydroxy-4-(3-trifluoromethyl-phenyl)-butyl)-1-(6-(2H-tetrazol-5-yl)-hexyl)-pyrrolidin-2-one.

This invention is also particularly directed to 7-{2S-[3R-hydroxy-4-(3-phenoxy-phenyl)-butyl]-5-oxo-pyrrolidin-1-yl}-heptanoic acid.

This invention is also particularly directed to 5S-(4-(3-chloro-phenyl)-3R-hydroxy-butyl)-1-(6-(2H-tetrazol-5-yl)-hexyl-pyrrolidin-2-one.

This invention is also particularly directed to 7-(2S-(3R-hydroxy-4-(3-trifluoromethyl-phenyl)-butyl)-5-oxo-pyrrolidin-1-yl)-heptanoic acid.

This invention is also particularly directed to 7-{2S-[4-(3-chloro-phenyl)-3R-hydroxy-butyl]-5-oxo-pyrrolidin-1-yl}-heptanoic acid.

This invention is also particularly directed to 5S-(3R-hydroxy-4-(3-trifluoromethyl-phenyl)-butyl)-1-(6-(2H-tetrazol-5-yl)-hexyl)-pyrrolidin-2-one.

Other features and advantages will be apparent from the specification and claims which describe the invention.

DETAILED DESCRIPTION OF THE INVENTION

Any EP4 receptor selective agonist may be used as the EP4 receptor selective agonist of this invention. EP4 selective agonists are compounds which have an IC50 at the EP1, EP2 and EP3 receptor which is at least 10-fold greater than the IC50 at the EP4 receptor subtype. For example, 7-(2-(3-hydroxy-4-phenyl-butyl)-5-oxo-pyrrolidin-1-yl)-heptanoic acid is an EP4 receptor selective PGE2 agonist with an EP4 receptor binding IC50 of 16 nM. At all other EP receptor subtypes, including the EP1, EP2 and EP3 receptor subtypes, the IC50 for 7-(2-(3-hydroxy-4-phenyl-butyl)-5-oxo-pyrrolidin-1-yl)-heptanoic acid is greater than 3200 nM.

The compounds of Formula I may be prepared as disclosed in commonly assigned U.S. Pat. No. 4,177,346, which is incorporated herein by reference.

The EP4 receptor selective agonists used in the methods of this invention are all adapted to therapeutic use as agents that stimulate bone formation and increase bone mass in a vertebrates, e.g., mammals, and particularly humans. Since bone formation is closely related to the development of osteoporosis and bone related disorders, the agonists used in the methods of this invention, by virtue of their action on bone, prevent, arrest and/or regress osteoporosis.

The utility of the EP4 selective agonists used in the methods of the present invention as medical agents in the treatment of conditions which present with low bone mass (e.g., osteoporosis) in vertebrates, e.g., mammals (especially humans and particularly female humans) is demonstrated by the activity of those agonists in conventional assays, including a receptor binding assay, a cyclic AMP assay, an in vivo assay and a fracture healing assay, all of which are described below. Such assays also provide a means whereby the activities of the EP4 selective agonists can be compared to each other and with the activities of other known compounds and compositions. The results of these comparisons are useful for determining dosage levels in a vertebrates, e.g., mammals, including humans, for the treatment of such diseases.

In Vivo Assay

The activity of anabolic bone agents in stimulating bone formation and increasing bone mass can be tested in intact male or female rats, sex hormone deficient male (orchidectomy) or female (ovariectomy) rats.

Male or female rats at different ages (such as 3 months of age) can be used in the study. The rats are either intact or castrated (ovariectomized or orchidectomized), and subcutaneously injected or gavaged with prostaglandin agonists at different doses (such as 1, 3, or 10 mg/kg/day) for 30 days. In the castrated rats, treatment is started at the next day after surgery (for the purpose of preventing bone loss) or at the time bone loss has already occured (for the purpose of restoring bone mass). During the study, all rats are allowed free access to water and a pelleted commercial diet (Teklad Rodent Diet #8064, Harlan Teklad, Madison, Wis.) containing 1.46% calcium, 0.99% phosphorus and 4.96 IU/g of Vitamin $D_3$. All rats are given subcutaneous injections of 10 mg/kg calcein on days 12 and 2 before sacrifice. The rats are sacrificed. The following endpoints are determined:

Femoral Bone Mineral Measurements

The right femur from each rat is removed at autopsy and scanned using dual energy X-ray absorptiometry (DXA, QDR 1000/W, Hologic Inc., Waltham, Mass.) equipped with "Regional High Resolution Scan" software (Hologic Inc., Waltham, Mass.). The scan field size is 5.08×1.902 cm, resolution is 0.0254×0.0127 cm and scan speed is 7.25 mm/second. The femoral scan images are analyzed and bone area, bone mineral content (BMC), and bone mineral density (BMD) of whole femoral (WF), distal femoral metaphyses (DFM), femoral shaft (FS), and proximal femora (PF) are determined.

Tibial Bone Histomorphometric Analyses

The right tibia is removed at autopsy, dissected free of muscle, and cut into three parts. The proximal tibia and the tibial shaft are fixed in 70% ethanol, dehydrated in graded concentrations of ethanol, defatted in acetone, then embedded in methyl methacrylate (Eastman Organic Chemicals, Rochester, N.Y.).

Frontal sections of proximal tibial metaphyses at 4 and 10 $\mu$m thickness are cut using a Reichert-Jung Polycut S microtome. The 4 $\mu$m sections are stained with modified Masson's Trichrome stain while the 10 $\mu$m sections remain unstained. One 4 $\mu$m and one 10 $\mu$m sections from each rat are used for cancellous bone histomorphometry.

Cross sections of tibial shaft at 10 $\mu$m thickness are cut using a Reichert-Jung Polycut S microtome. These sections are used for cortical bone histomorphometric analysis.

Cancellous bone histomorphometry: A Bioquant OS/2 histomorphometry system (R&M Biometrics, Inc., Nashville, Tenn.) is used for the static and dynamic histomorphometric measurements of the secondary spongiosa of the proximal tibial metaphyses between 1.2 and 3.6 mm distal to the growth plate-epiphyseal junction. The first 1.2 mm of the tibial metaphyseal region needs to be omitted in order to restrict measurements to the secondary spongiosa. The 4 $\mu$m sections are used to determine indices related to bone volume, bone structure, and bone resorption, while the 10 $\mu$m sections are used to determine indices related to bone formation and bone turnover.

I) Measurements and calculations related to trabecular bone volume and structure: (1) Total metaphyseal area (TV, $mm^2$): metaphyseal area between 1.2 and 3.6 mm distal to the growth plate-epiphyseal junction. (2) Trabecular bone area (BV, $mm^2$): total area of trabeculae within TV. (3) Trabecular bone perimeter (BS, mm): the length of total perimeter of trabeculae. (4) Trabecular bone volume (BV/TV, %): BV/TV×100. (5) Trabecular bone number (TBN, #/mm): 1.199/2×BS/TV. (6) Trabecular bone thickness (TBT, $\mu$m): (2000/1.199)×(BV/BS). (7) Trabecular bone separation (TBS, $\mu$m): (2000×1.199)×(TV-BV).

II) Measurements and calculations related to bone resorption: (1) Osteoclast number (OCN, #): total number of osteoclast within total metaphyseal area. (2) Osteoclast perimeter (OCP, mm): length of trabecular perimeter covered by osteoclast. (3) Osteoclast number/mm (OCN/mm, #/mm): OCN/BS. (4) Percent osteoclast perimeter (%OCP, %): OCP/BS×100.

III) Measurements and calculations related to bone formation and turnover: (1) Single-calcein labeled perimeter (SLS, mm): total length of trabecular perimeter labeled with one calcein label. (2) Double-calcein labeled perimeter (DLS, mm): total length of trabecular perimeter labeled with two calcein labels. (3) Inter-labeled width (ILW, $\mu$m): average distance between two calcein labels. (4) Percent mineralizing perimeter (PMS, %): (SLS/2+DLS)/BS×100. (5) Mineral apposition rate (MAR, $\mu$m/day): ILW/label interval. (6) Bone formation rate/surface ref. (BFR/BS, $\mu m^2/d/\mu m$): (SLS/2+DLS)×MAR/BS. (7) Bone turnover rate (BTR, %/y): (SLS/2+DLS)×MAR/BV×100.

Cortical bone histomorphometry: A Bioquant OS/2 histomorphometry system (R&M Biometrics, Inc., Nashville, Tenn.) is used for the static and dynamic histomorphometric measurements of tibial shaft cortical bone. Total tissue area, marrow cavity area, periosteal perimeter, endocortical perimeter, single labeled perimeter, double labeled perimeter, and interlabeled width on both periosteal and endocortical surface are measured, and cortical bone area (total tissue area—marrow cavity area), percent cortical bone area (cortical area/total tissue area×100), percent marrow area (marrow cavity area/total tissue area×100), periosteal and endocortical percent labeled perimeter [(single labeled perimeter/2+double labeled perimeter)/total perimeter×100], mineral apposition rate (interlabeled width/intervals), and bone formation rate [mineral apposition rate× [(single labeled perimeter/2+double labeled perimeter)/total perimeter] are calculated.

Statistics

Statistics can be calculated using StatView 4.0 packages (Abacus Concepts, Inc., Berkeley, Calif.). The analysis of variance (ANOVA) test followed by Fisher's PLSD (Stat View, Abacus Concepts Inc., 1918 Bonita Ave, Berkeley, Calif. 94704-1014) are used to compare the differences between groups.

Determination of cAMP Elevation in 293-S Cell Lines Stably Overexpressing Recombinant Human $EP_4$ Receptors cDNAs representing the complete open reading frames of the human $EP_4$ receptors are generated by reverse transcriptase polymerase chain reaction using oligonucleotide primers based on published sequences (1) and RNA from primary human lung cells ($EP_4$) as templates. cDNAs are cloned into the multiple cloning site of pcDNA3 (Invitrogen Corporation, 3985B Sorrento Valley Blvd., San Diego, Calif. 92121) and used to transfect 293-S human embryonic kidney cells via calcium phosphate co-precipitation. G418-resistant colonies are expanded and tested for specific [$^3$H] $PGE_2$ binding. Transfectants demonstrating high levels of specific [$^3$H]$PGE_2$ binding are further characterized by Scatchard analysis to determine Bmax and Kds for $PGE_2$. The lines selected for compound screening have approximately 256,400 receptors per cell and a Kd=2.9 nM for $PGE_2$ ($EP_4$). Constitutive expression of the receptor in parental 293-S cells is negligible. Cells are maintained in RPMI supplemented with fetal bovine serum (10% final) and G418 (700 ug/ml final).

cAMP responses in the 293-S/$EP_4$ lines are determined by detaching cells from culture flasks in 1 ml of Ca++ and Mg++ deficient PBS via vigorous pounding, adding serum-free RPMI to a final concentration of $1 \times 10^6$ cells/mI, and adding 3-isobutyl-1-methylxanthine (IBMX) to a final concentration of 1 mM. One milliliter of cell suspension is immediately aliquoted into individual 2 ml screwcap microcentrifuge and incubated for 10 minutes, uncovered, at 37° C., 5% $CO_2$, $_{95}$% relative humdity. The compound to be tested is then added to cells at 1:100 dilutions such that final DMSO or ethanol concentrations is 1%. Immediately after adding compound, the tubes are covered, mixed by inverting two times, and incubated at 37° C. for 12 minutes. Samples are then lysed by incubation at 100° C. for 10 minutes and immediately cooled on ice for 5 minutes. Cellular debris is pelleted by centrifugation at 1000×g for 5 minutes, and cleared lysates are transferred to fresh tubes. cAMP concentrations are determined using a commercially available cAMP radioimmunoassay kit RIA (NEK-033, DuPont/NEN Research Products, 549 Albany St., Boston, Mass. 02118) after diluting cleared lysates 1:10 in cAMP RIA assay buffer (included in kit). Typically, the cells are treated with 6–8 concentrations of the compound to be tested in 1 log increments. EC50 calculations are performed on a calculator using linear regression analysis on the linear portion of the dose response curves.

References

1. Regan, J. W. Bailey, T. J. Pepper, D. J. Pierce, K. L. Bogardus, A. M. Donello, J. E. Fairbairn, C. E. Kedzie, K. M. Woodward, D. F. and Gil, D. W. 1994 Cloning of a Novel Human Prostaglandin Receptor with Characteristics of the Pharmaclogically Defined $EP_2$ Subtype. Mol. Pharmacology 46:213–220.

Assay for Binding to Prostaglandin E2 Receptors

Membrane Preparation: All operations are performed at 4° C. Transfected cells expressing prostagiandin $E_2$ type 1 receptors ($EP_1$), type 2 ($EP_2$), type 3 ($EP_3$) or type 4 ($EP_4$) receptors are harvested and suspended to 2 million cells per ml in Buffer A [50 mM Tris-HCl (pH 7.4), 10 mM $MgCl_2$, 1 mM EDTA, 1 mM Pefabloc peptide, (Boehringer Mannheim Corp., Indianapolis, Ind.), 10 uM Phosporamidon peptide, (Sigma, St. Louis, Mo.), 1 uM pepstatin A peptide, (Sigma, St. Louis, Mo.), 10 uM elastatinal peptide, (Sigma, St. Louis, Mo.), 100 uM antipain peptide, (Sigma, St. Louis, Mo.)]. The cells are lysed by sonification with a Branson Sonifier (Model #250, Branson Ultrasonics Corporation, Danbury, Conn.) in 2 fifteen second bursts. Unlysed cells and debris are removed by centrifugation at 100×g for 10 min. Membranes are then harvested by centrifugation at 45,000×g for 30 minutes. Pelleted membranes are resuspended to 3–10 mg of protein per ml of Buffer A, the protein concentration being determined by the method of Bradford [Bradford, M., Anal. Biochem., 72, 248 (1976)]. Resuspended membranes are then stored frozen at −80° C. until use.

Binding Assay: Frozen membranes prepared as above are thawed and diluted to 0.5 mg/ml (for rat EP2) or 0.3 mg/ml (for rat EP4) in Buffer A above. Frozen membranes prepared as above are thawed and diluted to 0.5 mg/ml (for rat EP2) or 0.3 mg/ml (for rat EP4) in Buffer A above. One volume of membrane preparation is combined with 0.05 volume test compound or buffer and one volume of 3 nM $^3$H-prostaglandin $E_2$ (#TRK 431, Amersham, Arlington Heights, Ill.) in Buffer A. The mixture (205 μL total volume) is incubated for 1 hour at 25° C. The membranes are then recovered by filtration through type GF/C glass fiber filters (#1205-401, Wallac, Gaithersburg, Md.) using a Tomtec harvester (Model Mach II/96, Tomtec, Orange, Conn.). The membranes with bound $^3$H-prostaglandin $E_2$ are trapped by the filter, while the buffer and unbound $^3$H-prostaglandin $E_2$ pass through the filter into waste. Each sample is then washed 3 times with 3 ml of 50 mM Tris-HCl (pH 7.4), 10 mM $MgCl_2$, 1 mM EDTA. The filters are then dried by heating in a microwave oven. To determine the amount of $^3$H-prostaglandin bound to the membranes, the dried filters are placed into plastic bags with scintillation fluid and counted in a LKB 1205 Betaplate reader (Wallac, Gaithersburg, Md.). IC50s are determined from the concentration of test compound required to displace 50% of the specifically bound $^3$H-prostaglandin $E_2$.

293S cells expressing either the rat EP2 or EP4 prostaglandin $E_2$ receptors are generated according to methods known to those skilled in the art. Typically, PCR (polymerase chain reaction) primers corresponding to the 5' and 3' ends of the published full length receptor are made according to well known methods disclosed above and are used in an RT-PCR reaction using total RNA from rat kidney for both EP2 and EP4 receptors.

The full length coding sequence for the rat EP2 receptor is made as disclosed in Nemoto et al., Prostaglandins, 1997, 54, 713–725. The full length coding sequence for the rat EP4 receptor is made as disclosed in Sando et al., Biochem. Biophys. Res. Comm., 1994, 200, 1329–1333. These full length receptors are used to prepare 293S cells expressing the EP2 and EP4 receptors.

The full length coding sequence for the $EP_1$ receptor is made as disclosed in Funk et al., Journal of Biological Chemistry, 1993, 268, 26767–26772. The full length coding sequence for the $EP_2$ receptor is made as disclosed in Regan et al., Molecular Pharmacology, 1994, 46, 213–220. The full length coding sequence for the $EP_3$ receptor is made as disclosed in Regan et al., British Journal of Pharmacology, 1994, 112, 377–385. The full length coding sequence for the $EP_4$ receptor is made as disclosed in Bastien, Journal of Biological Chemistry, 1994, 269, 11873–11877. These full length receptors are used to prepare 293S cells expressing the $EP_1$, $EP_2$, $EP_3$ and $EP_4$ receptors.

293S cells expressing either the human $EP_1$, $EP_2$, $EP_3$ or $EP_4$ prostaglandin $E_2$ receptors are generated according to methods known to those skilled in the art. Typically, PCR (polymerase chain reaction) primers corresponding to the 5' and 3' ends of the published full length receptor are made according to the well known methods disclosed above and are used in an RT-PCR reaction using the total RNA from human kidney (for $EP_1$), human lung (for $EP_2$), human lung (for $EP_3$) or human lymphocytes (for $EP_4$) as a source. PCR products are cloned by the TA overhang method into pCR2.1 (Invitrogen, Carlsbad, Calif.) and identity of the cloned receptor is confirmed by DNA sequencing.

293S cells (Mayo, Dept. of Biochemistry, Northwestern Univ.) are transfected with the cloned receptor in pcDNA3 by electroporation. Stable cell lines expressing the receptor are established following selection of transfected cells with G418.

Clonal cell lines expressing the maximal number of receptors are chosen following a whole cell $^3$H-$PGE_2$ binding assay using unlabeled $PGE_2$ as a competitor.

Fracture Healing Assays Assay For Effects on Fracture Healing After Systemic Administration Fracture Technique: Sprage-Dawley rats at 3 months of age are anesthetized with Ketamine. A 1 cm incision is made on the anteromedial aspect of the proximal part of the right tibia or femur. The following describes the tibial surgical technique. The incision is carried through to the bone, and a 1 mm hole is drilled 4 mm proximal to the distal aspect of the tibial tuberosity 2 mm medial to the anterior ridge. Intramedullary nailing is performed with a 0.8 mm stainless steel tube (maximum load 36.3 N, maximum stiffness 61.8 N/mm, tested under the same conditions as the bones). No reaming of the medullary canal is performed. A standardized closed fracture is produced 2 mm above the tibiofibular junction by three-point bending using specially designed adjustable forceps with blunt jaws. To minimize soft tissue damage, care is taken not to displace the fracture. The skin is closed with monofilament nylon sutures. The operation is performed under sterile conditions. Radiographs of all fractures are taken immediately after nailing, and rats with fractures outside the specified diaphyseal area or with displaced nails are excluded. The remaining animals are divided randomly into the following groups with 10–12 animals per each subgroup per time point for testing the fracture healing. The first group receives daily gavage of vehicle (water: 100% Ethanol=95:5) at 1 ml/rat, while the others receive daily gavage from 0.01 to 100 mg/kg/day of the compound to be tested (1 ml/rat) for 10, 20, 40 and 80 days.

At 10, 20, 40 and 80 days, 10–12 rats from each group are anesthetized with Ketamine and sacrificed by exsanguination. Both tibiofibular bones are removed by dissection and all soft tissue is stripped. Bones from 5–6 rats for each group are stored in 70% ethanol for histological analysis, and bones from another 5–6 rats for each group are stored in a buffered Ringer's solution (+4° C., pH 7.4) for radiographs and biomechanical testing which is performed.

Histological Analysis: The methods for histologic analysis of fractured bone have been previously published by Mosekilde and Bak (The Effects of Growth Hormone on Fracture Healing in Rats: A Histological Description. Bone, 14:19–27, 1993). Briefly, the fracture site is sawed 8 mm to each side of the fracture line, embedded undecalcified in methymethacrylate, and cut frontals sections on a Reichert-Jung Polycut microtome in 8 μm thick. Masson-Trichrome stained mid-frontal sections (including both tibia and fibula) are used for visualization of the cellullar and tissue response to fracture healing with and without treatment. Sirius red stained sections are used to demonstrate the characterisitics of the callus structure and to differentiate between woven bone and lamellar bone at the fracture site. The following measurements are performed: (1) fracture gap—measured as the shortest distance between the cortical bone ends in the fracture, (2) callus length and callus diameter, (3) total bone volume area of callus, (4) bony tissue per tissue area inside the callus area, (5) fibrous tissue in the callus, and (6) cartilage area in the callus.

Biomechanical Analysis: The methods for biomechanical analysis have been previously published by Bak and Andreassen (The Effects of Aging on Fracture Healing in Rats. Calcif Tissue Int 45:292–297, 1989). Briefly, radiographs of all fractures are taken prior to the biomechanical test. The mechanical properties of the healing fractures are analyzed by a destructive three- or four-point bending procedure. Maximum load, stiffness, energy at maximum load, deflection at maximum load, and maximum stress are determined.

Assay for Effects on Fracture Healing After Local Administration

Fracture Technique: Female or male beagle dogs at approximately 2 years of age are used under anesthesia in the study. Transverse radial fractures are produced by slow continuous loading in three-point bending as described by Lenehan et al. (Lenehan, T. M.; Balligand, M.; Nunamaker, D. M.; Wood, F. E.: Effects of EHDP on Fracture Healing in Dogs. J Orthop Res 3:499–507; 1985). A wire is pulled through the fracture site to ensure complete anatomical disruption of the bone. Thereafter, local delivery of prostaglandin agonists to the fracture site is achieved by slow release of compound delivered by slow release pellets or by administration of the compounds in a suitable formulation such as a paste gel solution or suspension for 10, 15, or 20 weeks.

Histological Analysis: The methods for histologic analysis of fractured bone have been previously published by Peter et al. (Peter, C. P.; Cook, W. O.; Nunamaker, D. M.; Provost, M. T.; Seedor, J. G.; Rodan, G. A. Effects of alendronate on fracture healing and bone remodeling in dogs. J. Orthop. Res. 14:74–70, 1996) and Mosekilde and Bak (The Effects of Growth Hormone on Fracture Healing in Rats: A Histological Description. Bone, 14:19–27, 1993). Briefly, after sacrifice, the fracture site is sawed 3 cm to each side of the fracture line, embedded undecalcified in methymethacrylate, and cut on a Reichert-Jung Polycut microtome in 8 μm thick of frontal sections. Masson-Trichrome stained mid-frontal sections (including both tibia and fibula) are used for visualization of the cellullar and tissue response to fracture healing with and without treatment. Sirius red stained sections are used to demonstrate the characterisitics of the callus structure and to differentiate between woven bone and lamellar bone at the fracture site. The following measurements are performed: (1) fracture gap—measured as the shortest distance between the cortical bone ends in the fracture, (2) callus length and callus diameter, (3) total bone volume area of callus, (4) bony tissue per tissue area inside the callus area, (5) fibrous tissue in the callus, (6) cartilage area in the callus.

Biomechanical Analysis: The methods for biomechanical analysis have been previously published by Bak and Andreassen (The Effects of Aging on Fracture Healing in Rats. Calcif Tissue Int 45:292–297, 1989) and Peter et al. (Peter, C. P.; Cook, W. O.; Nunamaker, D. M.; Provost, M. T.; Seedor, J. G.; Rodan, G. A. Effects of Alendronate On Fracture Healing And Bone Remodeling In Dogs. J. Orthop. Res. 14:74–70, 1996). Briefly, radiographs of all fractures are taken prior to the biomechanical test. The mechanical properties of the healing fractures are analyzed by a destructive three- or four-point bending procedures. Maximum load, stiffness, energy at maximum load, deflection at maximum load, and maximum stress are determined.

Administration of the EP4 receptor selective agonists according to the methods of this invention can be via any mode which delivers the EP4 receptor selective agonist systemically and/or locally (e.g., at the site of the bone fracture, osteotomy, or orthopedic surgery). These methods include oral routes, parenteral, intraduodenal routes, etc. Generally, the compounds of this invention are administered orally, but parenteral administration (e.g., intravenous, intramuscular, transdermal, subcutaneous, rectal or intramedullary) may be utilized, for example, where oral administration is inappropriate for the target or where the patient is unable to ingest the drug.

The methods of this invention are used for the treatment and promotion of healing of bone fractures and osteotomies by the local application (e.g., to the sites of bone fractures of osteotomies) of EP4 receptor selective agonists. The EP4 receptor selective agonists of this invention are applied to the sites of bone fractures or osteotomies, for example, either by injection of the compound in a suitable solvent (e.g., an oily solvent such as arachis oil) to the cartilage growth plate or, in cases of open surgery, by local application thereto of the compound in a suitable vehicle, carrier or diluent such as bone-wax, demineralized bone powder, polymeric bone cements, bone sealants, etc. Alternatively, local application can be achieved by applying a solution or dispersion of the compound in a suitable carrier or diluent onto the surface of, or incorporating it into solid or semi-solid implants conventionally used in orthopedic surgery, such as dacron-mesh, gel-foam and kiel bone, or prostheses.

In any event, the amount and timing of compounds administered will, of course, be dependent on the subject being treated, on the severity of the affliction, on the manner of administration and on the judgment of the prescribing physician. Thus, because of patient to patient variability, the dosages given herein are a guideline and the physician may titrate doses of the drug compound to achieve the treatment (e.g., bone mass augmentation) that the physician considers appropriate for the patient. In considering the degree of treatment desired, the physician must balance a variety of factors such as bone mass starting level, age of the patient, presence of preexisting disease, as well as presence of other diseases (e.g., cardiovascular disease).

In general an amount of an EP4 receptor selective agonist is used that is sufficient to augment bone mass to a level which is above the bone fracture threshold (as detailed in the World Health Organization Study previously cited herein).

The EP4 receptor selective agonist compounds used in the methods of this invention are generally administered in the form of a pharmaceutical composition comprising at least one of the compounds of this invention together with a pharmaceutically acceptable vehicle or diluent. Thus, the EP4 receptor selective agonist can be administered individually in any conventional oral, intranasal, parenteral, rectal or transdermal dosage form.

For oral administration the pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compositions of this invention can be combined with various sweetening agents, flavoring agents, coloring agents, emulsifying agents and/or suspending agents, as well as such diluents as water, ethanol, propylene glycol, glycerin and various like combinations thereof.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of transdermal (e.g.,topical) administration, dilute sterile, aqueous or partially aqueous solutions (usually in about 0.1% to 5% concentration), otherwise similar to the above parenteral solutions, are prepared.

Methods of preparing various pharmaceutical compositions with a certain amount of active ingredient are known, or will be apparent in light of this disclosure, to those skilled in the art. For examples of methods of preparing pharmaceutical compositions, see *Remington's Pharmaceutical Sciences*, Mack Publishing Company, Easton, Pa., 19th Edition (1995).

Study Protocol

The purpose of this study is to determine whether an EP4 receptor selective agonist, and specifically 7-(2-(3-hydroxy-4-phenyl-butyl)-5-oxo-pyrrolidin-1-yl)-heptanoic acid, can restore bone mass in OVX rat model.

Sprague-Dawley male rats were ovariectomized (OVX) at 3.5 months of age. Ten months after OVX, the rats were treated by subcutaneous injection with vehicle or 7-(2-(3-hydroxy-4-phenyl-butyl)-5-oxo-pyrrolidin-1-yl)-heptanoic acid at 30 mg/kg/day for 28 days. The rats were autopsied. The right femur from each rat was removed at autopsy and scanned using dual energy x-ray absorptiometry (DEXA, QDR 1000/W, Hologic Inc., Waltham, Mass.) equipped with "Regional High Resolution Scan" software (Hologic Inc., Waltham, Mass.). The scan field size was 5.08×1.902 cm, resolution is 0.0254×0.0127 cm and the scan speed was 7.25 mm/second. The femoral scan images were analyzed. Bone mineral content (BMC) and bone mineral density (BMD) of whole femora (WF), distal femoral metaphysis (DFM), and femoral shaft (FS) were determined according to the method described in H. Z. Ke et al., Droloxifene, a New Estrogen Antagonist/Agonist, Prevents Bone Loss in Ovariectomized Rats. ENDOCRINOLOGY 136;2435–2441, 1995.

Study Results and Discussion

Compared with OVX rats treated with vehicle, OVX rats treated with 7-(2-(3-hydroxy-4-phenyl-butyl)-5-oxo-pyrrolidin-1-yl)-heptanoic acid showed total femoral BMC increased by 17%, total femoral BMD increased by 13%, distal femoral BMC increased by 8%, distal femoral BMD increased by 8%, femoral shaft BMC increased by 20%, and femoral shaft BMD increased by 18%. No PGE2-like side effects were seen in rats treated with 7-(2-(3-hydroxy-4-phenyl-butyl)-5-oxo-pyrrolidin-1-yl)-heptanoic acid.

This data shows that 7-(2-(3-hydroxy-4-phenyl-butyl)-5-oxo-pyrrolidin-1-yl)-heptanoic acid, an EP4 receptor selective PGE2 agonist, stimulates bone formation and restores bone in established osteopenic OVX rats.

General Experimental Procedures

NMR spectra were recorded on a Varian Unity 400 spectrometer (Varian Co., Palo Alto, Calif.) at about 23° C. at 400 MHz for proton nuclei. Chemical shifts are expressed in parts per million. The peak shapes are denoted as follows: s, singlet; d, doublet; t, triplet; q, quartet; m, multiplet; bs=broad singlet. Atmospheric pressure chemical ionization (APCI) mass spectra were obtained on a Fisons Platform II Spectrometer. Where the intensity of chlorine or bromine-containing ions are described the expected intensity ratio was observed (approximately 3:1 for $^{35}Cl/^{37}Cl$-containing ions) and 1:1 for $^{79}Br/^{81}Br$-containing ions) and the intensity of only the lower mass ion is given.

Medium pressure chromatography was performed using a Biotage purification system (Biotage, Dyax Corporation, Charlottesville, Va.) under nitrogen pressure. Flash chromatography was performed with either Baker Silica Gel (40 □m) (J. T. Baker, Phillipsburg, N.J.) or Silica Gel 60 (EM Sciences, Gibbstown, N.J.) in glass columns under low nitrogen pressure. Radial Chromatography was performed using a Chromatotron (model 7924T, Harrison Research). Preparative Chromatography was performed using Analtech Uniplates Silica Gel GF (20×20 cm) (Analtech, Inc. Newark, Del.). Dimethylformamide (DMF), tetrahydrofuran (THF), and dichloromethane ($CH_2Cl_2$) used as reaction solvents were the anhydrous grade supplied by Aldrich Chemical Company (Milwaukee, Wis.). The term 'concentrated' refers to removal of solvent at water aspirator pressure on a rotary evaporator. The abbreviation "h" stands for hours. The term "TBAF" refers to tetrabutylammonium fluoride. The term "DMAP" refers to dimethylaminopyridine. The terms "dichloromethane" and "methylene chloride" are synonymous and are used interchangeably throughout this specification and in the Examples and Preparations.

EXAMPLE 1

7-{2S-[4-(3-Chloro-phenyl)-3R-hydroxy-butyl]-5-oxo-pyrrolidin-1-yl}-heptanoic acid

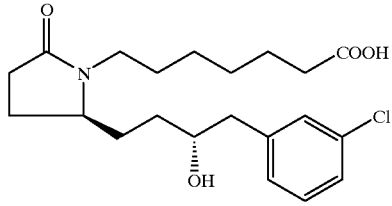

Step A: 7-{2R-[4-(3-Chloro-phenyl)-3-oxo-but-1-enyl]-5-oxo-pyrrolidin-1-yl}-heptanoic acid ethyl ester To a solution of [3-(3-chloro-phenyl)-2-oxo-propyl]-phosphonic acid dimethyl ester (2.66 g, 9.63 mmol) in THF (35 mL) at 0° C. was added NaH (60% by weight in oil, 426 mg, 10.7 mmol) portionwise. The reaction mixture was stirred at room temperature for 40 minutes. The reaction mixture was cooled to 0° C. and a solution of 7-(2R-formyl-5-oxo-pyrrolidin-1-yl)-heptanoic acid ethyl ester (assumed 10.6 mmol, prepared according to the method described in Preparation 7, but using different amounts of reagents) in THF was added and the reaction was stirred for 18 h. AcOH was added and the reaction mixture was diluted with EtOAc. The organic solution was washed consecutively with saturated NaHCO₃ solution (2×), water (1×), and brine (1×). The organic solution was dried (MgSO₄), filtered and concentrated. The residue was purified by medium pressure chromatography eluting with 15% acetone in toluene to provide 7-{2R-[4-(3-chloro-phenyl)-3-oxo-but-1-enyl]-5-oxo-pyrrolidin-1-yl}-heptanoic acid ethyl ester (2.26 g). ¹H NMR (CDCl₃) δ7.27–7.15 (m, 3H), 7.08 (m, 1H), 6.66 (dd, 1H), 6.20 (d, 1H), 4.17 (m, 1H), 4.11 (q, 2H), 3.82 (s, 2H), 3.55 (m, 1H), 2.72 (m, 1H), 2.46–2.23 (m, 5H), 1.79 (m, 1H), 1.58 (m, 2H), 1.47–1.20 (m, 9H); MS 420.2 (M+1), 418.2 (M−1).

Step B: 7-{2R -[4-(3-Chloro-phenyl)-3S-hydroxy-but-1-enyl]-5-oxo-pyrrolidin-1-yl}-heptanoic acid ethyl ester To a solution of 7-{2R -[4-(3-chloro-phenyl)-3-oxo-but-1-enyl]- 5-oxo-pyrrolidin-1-yl}-heptanoic acid ethyl ester (2.1 g, 5.0 mmol) in anhydrous CH₂Cl₂ (200 mL) was added (R)-2-methyl-CBS-oxazaborolidine (1M in toluene, 5 mL, 5 mmol) and the solution was cooled to −45° C. The reaction mixture was stirred for 20 minutes and catecholborane (1M in THF, 15 mL, 15 mmol) was added. The reaction mixture was stirred for 18 h at −45° C. Aqueous HCl (1N, 100 mL) was added and the reaction mixture was stirred at room temperature for 18 h. The acidic aqueous layer was separated and the organic solution was washed with ice-cold 1N NaOH (2×) followed by brine (1×). The organic solution was dried (MgSO₄), filtered and concentrated. Purification by medium pressure chromatography (1:1 EtOAc:hexanes to 80% EtOAc in hexanes) provided 7-{2R -[4-(3-chloro-phenyl)-3S-hydroxy-but-1 -enyl]-5-oxo-pyrrolidin-1-yl}-heptanoic acid ethyl ester (800 mg) as an approximate 6:1 mixture of 3S:3R alcohol diastereomers by ¹H NMR. ¹H NMR (CDCl₃) δ7.23–7.17 (m, 3H), 7.06 (m, 1H), 5.67 (dd, 1H), 5.46 (dd, 1H), 4.37 (m, 1H), 4.08 (q, 2H), 4.00 (m,1H), 3.44 (m, 1H), 2.80 (m, 2H), 2.67 (m, 1H), 2.41–2.12 (m, 5H), 1.70–1.20 (m, 13H); MS 422.3 (M+1).

Step C: 7-{2S-[4-(3-Chloro-phenyl)-3R-hydroxy-butyl]-5-oxo-pyrrolidin-1-yl}-heptanoic acid ethyl ester To a solution of 7-{2R-[4-(3-chloro-phenyl)-3S-hydroxy-but-1-enyl]-5-oxo-pyrrolidin-1-yl}-heptanoic acid ethyl ester (800 mg, 1.90 mmol) in EtOH (50 mL) was added 10% palladium on carbon (80 mg). The reaction mixture was hydrogenated on a Parr shaker at 45 psi for for 4.5 h. The catalyst was removed via filtration through Celite® with the aid of EtOH. Purification by medium pressure chromatography (1:1 hexanes:EtOAc to 4:1 EtOAc:hexanes) provided 7-{2S-[4-(3-chloro-phenyl)-3R-hydroxy-butyl]-5-oxo-pyrrolidin-1-yl}-heptanoic acid ethyl ester (625 mg). ¹H NMR (CDCl₃) δ7.27–7.21 (m, 3H), 7.09 (m, 1H), 4.10 (m, 2H), 3.84 (m, 1H), 3.61 (m, 2H), 2.90 (m, 1H), 2.78 (dd, 1H), 2.68 (m, 1H), 2.47–2.25 (m, 4H), 2.12 (m, 1H), 1.92–1.22 (m, 17H); MS 424.3 (M+1).

Step D: 7-{2S-[4-(3-Chloro-phenyl)-3R-hydroxy-butyl]-5-oxo-pyrrolidin-1-yl}-heptanoic acid To a solution of 7-{2S-[4-(3-chloro-phenyl)-3R-hydroxy-butyl]-5-oxo-pyrrolidin-1 -yl}-heptanoic acid ethyl ester (595 mg, 1.40 mmol) in ETOH (25 mL) was added 2N NaOH (6 mL). The reaction was stirred for 24 h at room temperature and was concentrated in vacuo to about ¾ the original volume. Aqueous 1N HCl was added to obtain a pH of about 2. The aqueous solution was washed with methylene chloride (3×). The combined organic layers were washed with water followed by brine. The organic solution was dried (MgSO₄), filtered and concentrated to provide the title compound of Example 1 (500 mg). ¹H NMR (CDCl₃) δ7.26–7.18 (m, 3H), 7.08 (m, 1H), 3.84 (m, 1H), 3.58 (m, 2H), 2.90 (m, 1H), 2.77 (dd, 1H), 2.68 (m, 1H), 2.43–2.28 (m, 4H), 2.10 (m, 1H), 1.78 (m, 1H), 1.66–1.22 (m, 13H); MS 396.2 (M+1), 394.2 (M−1).

EXAMPLE 2

7-{2S-[3R-Hydroxy-4-(3-trifluoromethyl-phenyl)-butyl]-5-oxo-pyrrolidin-1-yl}-heptanoic acid

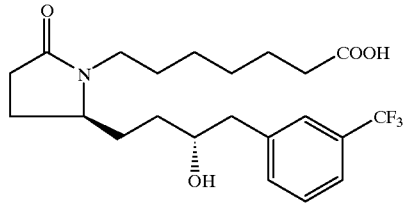

Step A: 7-{2-Oxo-5R-[3-oxo-4-(3-trifluoromethyl-phenyl)-but-1-enyl]-pyrrolidin-1 -yl}-heptanoic acid ethyl ester Following the procedure described for Example 1, Step A, the anion derived from [2-oxo-3-(3-trifluoromethyl-phenyl)-propyl]-phosphonic acid dimethyl ester (4.16 g, 13.40 mmol) and NaH (60% in oil, 590 mg, 14.7 mmol) was reacted with 7-(2R-formyl-5-oxo-pyrrolidin-1-yl)-heptanoic acid ethyl ester (assumed 14.74 mmol) over 24 h. Purification by medium pressure chromatography (solvent gradient 20% EtOAc in hexanes to EtOAc) provided 7-{2-oxo-5R-[3-oxo-4-(3-trifluoromethyl-phenyl)-but-1-enyl]-pyrrolidin-1-yl}-heptanoic acid ethyl ester (4.29 g). ¹H NMR (CDCl₃) δ7.52 (d, 1H), 7.44 (m, 2H), 7.37 (d, 1H), 6.67 (dd, 1H), 6.67 (dd, 1H), 6.22 (d, 1H), 4.80 (m, 1H), 4.08 (q, 2H), 3.90 (s, 2H), 3.54 (m, 1H), 2.70 (m, 1H), 2.37 (m, 2H), 2.24 (m, 3H), 1.78 (m, 1H), 1.56 (m, 2H), 1.44–1.20 (m, 9H); MS 454.2 (M+1) 452.2 (M−1).

Step B: 7-{2R-[3S-Hydroxy-4-(3-trifluoromethyl-phenyl)-but-1-enyl]-5-oxo-pyrrolidin-1-yl}-heptanoic acid ethyl ester To a solution of 7-{2-oxo-5R-[3-oxo-4-(3-trifluoromethyl-phenyl)-but-1-enyl]-pyrrolidin-1-yl}-heptanoic acid ethyl ester (1.5 g, 3.31 mmol) and (R)-2-methyl-CBS-oxazaborolidine (1M in toluene, 0.5 mL, 0.5 mmol) in CH₂Cl₂ (100 mL) at −45° C. was added catecholborane (1M in THF, 9.9 mL, 9.9 mmol) dropwise. The solution was stirred for 24 h at −45° C. and 1N HCl was added. The reaction mixture was stirred at room temperature for 1 h and the layers were separated. The aqueous solution was washed with CH₂Cl₂ (2×) and the combined organic layers were washed consecutively with ice-cold 0.5N NaOH and brine (two times). The organic solution was dried (MgSO₄), filtered and concentrated. Purification by medium pressure chromatography (50% EtOAc in hexanes to 60% EtOAc in hexanes to 80% EtOAc in hexanes to EtOAc to 5% MeOH in CH₂Cl₂) provided 7-{2R-[3S-hydroxy-4-(3-trifluoromethyl-phenyl)-but-1-enyl]-5-oxo-pyrrolidin-1-yl}-heptanoic acid ethyl ester (1.23 g) as an approximate 5.5:1 mixture of 3S:3R alcohol diastereomers by HPLC analysis. ¹H NMR (CDCl₃) δ7.51–7.35 (m, 4H), 5.72 (dd, 1H), 5.50 (dd, 1H), 4.44 (m, 1H), 4.09 (q, 2H), 4.01 (m, 1H), 3.44 (m, 1H), 2.90 (d, 2H), 2.71 (m, 1H), 2.37–2.12 (m, 5H), 1.70–1.21 (m, 13H); MS 456.3 (M+1), 454.3 (M−1).

Step C: 7-{2S-[3R-Hydroxy-4-(3-trifluoromethyl-phenyl)-butyl]-5-oxo-pyrrolidin-1-yl}-heptanoic acid ethyl ester Following the procedure described for Example 1, Step C, a solution of 7-{2R-[3S-hydroxy-4-(3-trifluoromethyl-phenyl)-but-1-enyl]-5-oxo-pyrrolidin-1-yl}-heptanoic acid ethyl ester (1.18 g, 2.59 mmol) in EtOH (50 mL) was hydrogenated in the presence of 10% palladium on carbon (120 mg) at 40–45 psi on a Parr shaker for 24 h. Purification by medium pressure chromatography (50% EtOAc in hexanes to EtOAc to 1% MeOH in CH₂Cl₂ to 3% MeOH in CH₂Cl₂ to 5% MeOH in CH₂Cl₂ to 10% MeOH in CH₂Cl₂) provided 7-{2S-[3R-hydroxy-4-(3-trifluoromethyl-phenyl)-butyl]-5-oxo-pyrrolidin-1-yl}-heptanoic acid ethyl ester (1.08 g). ¹H NMR (CDCl₃) δ7.51–7.39 (m, 4H), 4.09 (q, 2H), 3.86 (m, 1H), 3.60 (m, 2H), 2.89 (m, 2H), 2.76 (m, 1H), 2.33 (m, 4H), 2.11 (m, 1H), 1.80 (m, 1H), 1.68–1.21 (m, 16H).

Step D: 7-{2S-[3R-Hydroxy-4-(3-trifluoromethyl-phenyl)-butyl]-5-oxo-pyrrolidin-1-yl }-heptanoic acid Following the procedure described for Example 1, Step D, 7-{2S-[3R-hydroxy-4-(3-trifluoromethyl-phenyl)-butyl]-5-oxo-pyrrolidin-1-yl}-heptanoic acid ethyl ester (1.93 g, 4.22 mmol) was hydrolyzed with 6N NaOH (26 mL) in EtOH (52 mL) over 24 h. Purification by medium pressure chromatography (EtOAc to 1% MeOH in CH₂Cl₂ to 3% MeOH in CH₂Cl₂ to 5% MeOH in CH₂Cl₂ to 10% MeOH in CH₂Cl₂) provided 7-{2S-[3R-hydroxy-4-(3-trifluoromethyl-phenyl)-butyl]-5-oxo-pyrrolidin-1-yl }-heptanoic acid (1.66 g). ¹H NMR (CDCl₃) δ7.51–7.39 (m, 4H), 3.88 (m, 1H), 3.58 (m, 2H), 2.84 (m, 3H), 2.34 (m, 4H), 2.10 (m, 1H), 1.80 (m, 1H), 1.67–1.26 (m, 13H); MS 430.4 (M+1).

Step E: Sodium salt of 7-{2S-[3R-Hydroxy-4-(3-trifluoromethyl-phenyl)-butyl]-5-oxo-pyrrolidin-1-yl}-heptanoic acid To a solution of 7-{2S-[3R-hydroxy-4-(3-trifluoromethyl-phenyl)-butyl]-5-oxo-pyrrolidin-1-yl}-heptanoic acid (1.66 g, 3.87 mmol) in EtOH (16 mL) was added NaHCO₃ (325 mg, 3.87 mmol) in water (3 mL). The reaction mixture was stirred for 5 h and was concentrated in vacuo. The residue was azeotroped with CH₂Cl₂ (3×) to provide the sodium salt of the title compound of Example 2 (1.698 g). ¹H NMR (CD₃OD) δ7.48 (m, 4H), 3.80 (m, 1H), 3.69 (m, 1H), 3.52 (m, 1H), 2.94 (m, 1H), 2.81 (m, 2H), 2.32 (m, 2H), 2.13 (m, 3H), 1.81 (m, 1H), 1.69–1.26 (m, 13H); MS 430.3 (M−Na+1), 428.2 (M−Na−1).

EXAMPLE 3

5S-[4-(3-Chloro-phenyl)-3-hydroxy-butyl]-1-[6-(2H-tetrazol-5-yl)-hexyl ]-pyrrolidin-2-one

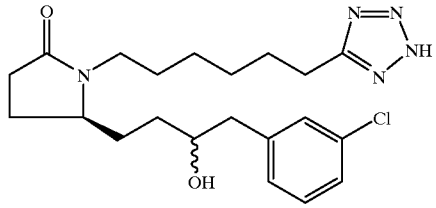

Step A: 7-{2R-[4-(3-Chloro-phenyl)-3-oxo-but-1-enyl]-5-oxo-pyrrolidin-1-yl }-heptanenitrile Following the procedure described for Example 1, Step A, the anion derived from [3-(3-chloro-phenyl)-2-oxo-propyl]-phosphonic acid dimethyl ester (3.35 g, 12.12 mmol) and NaH (60% in oil, 533 mg, 13.3 mmol) was reacted with 7-(2R-formyl-5-oxo-pyrrolidin-1-yl)-heptanenitrile (assumed 13.3 mmol) over 18 h. Purification by medium pressure chromatography (20% EtOAc in hexanes to 80% EtOAc in hexanes) provided 7-{2R-[4-(3-chloro-phenyl)-3-oxo-but-1-enyl]-5-oxo-pyrrolidin-1-yl}-heptanenitrile (1.52 g). $^1$H NMR (CDCl$_3$) δ7.24 (m, 2H), 7.17 (s, 1H), 7.06 (m, 1H), 6.64 (dd, 1H), 6.20 (d, 1H), 4.15 (m, 1H), 3.80 (s, 2H), 3.50 (m, 1H), 2.72 (m, 1H), 2.46–2.20 (m, 5H), 1.78 (m, 1H), 1.59 (m, 2H), 1.40 (m, 4H), 1.24 (m, 2H).

Step B: 7-{2S-[4-(3-Chloro-phenyl)-3-oxo-butyl]-5-oxo-pyrrolidin-1-yl}-heptanenitrile Following the procedure described for Example 1, Step C, 7-{2R-[4-(3-chloro-phenyl)-3-oxo-but-1-enyl]-5-oxo-pyrrolidin-1-yl}-heptanenitrile (860 mg, 2.31 mmol) in MeOH (40 mL) was hydrogenated in the presence of 10% palladium on carbon (86 mg) for 1 h. Purification by radial chromatography (hexanes to 20% EtOAc in hexanes to 70% EtOAc in hexanes) provided 7-{2S-[4-(3-chloro-phenyl)-3-oxo-butyl]-5-oxo-pyrrolidin-1-yl}-heptanenitrile (730 mg).

Step C: 7-{2S-[4-(3-Chloro-phenyl)-3-hydroxy-butyl]-5-oxo-pyrrolidin-1-yl }-heptanenitrile To a solution of 7-{2S-[4-(3-chloro-phenyl)-3-oxo-butyl]-5-oxo-pyrrolidin-1-yl}-heptanenitrile (730 mg, 1.87 mmol) in MeOH (30 mL) at 0° C. was added NaBH$_4$ (35 mg, 0.921 mmol). The reaction mixture was stirred at 0° C. for 45 minutes and water was added. The volatiles were removed in vacuo and the remaining aqueous solution was diluted with methylene chloride. The organic solution was washed with water followed by brine, dried (MgSO$_4$), filtered and concentrated. Purification by medium pressure chromatography (1:1 hexanes:EtOAc to EtOAc to 3% MeOH in CH$_2$Cl$_2$) provided 7-{2S-[4-(3-chloro-phenyl)-3-hydroxy-butyl]-5-oxo-pyrrolidin-1-yl}-heptanenitrile (730 mg). $^1$H NMR (CDCl$_3$) δ7.22 (m, 3H), 7.07 (d, 1H), 3.80 (m, 1H), 3.57 (m, 2H), 2.88 (m, 1H), 2.78 (m, 1H), 2.64 (m, 1H), 2.31 (m, 4H), 2.10 (m, 1H), 1.65–1.22 (m, 14H); MS 377.3 (M+1).

Step D: 5S-[4-(3-Chloro-phenyl)-3-hydroxy-butyl]-1-[6-(2H-tetrazol-5-yl)-hexyl]-pyrrolidin-2-one A solution of 7-{2S-[4-(3-chloro-phenyl)-3-hydroxy-butyl]-5-oxo-pyrrolidin-1-yl}-heptanenitrile (730 mg, 1.94 mmol), trimethylsilylazide (0.63 mL, 0.475 mmol) and dibutyltin oxide (96 mg, 3.87 mmol) in toluene (30 mL) was heated at reflux for 18 h. The volatiles were removed in vacuo and the residue was diluted with CH$_2$Cl$_2$. The organic solution was washed with 1N HCl followed by brine. The organic solution was dried (MgSO$_4$), filtered, and concentrated. The residue was purified by medium pressure chromatography eluting with EtOAc to 2% MeOH in CH$_2$Cl$_2$ to 7% MeOH in CH$_2$Cl$_2$ to give the TMS complex. The residue was diluted with MeOH and 2N HCl was added and the solution was stirred for 40 minutes. The solution was diluted with CH$_2$Cl$_2$ and the organic layer was washed with water followed by brine. The organic solution was dried (MgSO$_4$), filtered, and concentrated. The residue was purified by medium pressure chromatography eluting with EtOAc to 7% MeOH in CH$_2$Cl$_2$ to provide 5S-[4-(3-chloro-phenyl)-3-hydroxy-butyl]-1-[6-(2H-tetrazol-5-yl)-hexyl]-pyrrolidin-2-one (521 mg). $^1$H NMR (CDCl$_3$) δ7.23 (m, 3H), 7.09 (d, 1H), 3.85 (m, 1H), 3.66 (m, 1H), 3.53 (m, 1H), 2.96 (m, 3H), 2.81 (m, 1H), 2.70 (m, 1H), 2.44 (m, 2H), 2.18 (m, 1H), 1.88–1.27 (m, 14H); MS 420.2 (M+1), 418.3 (M−1).

EXAMPLE 4

5S-[3R-Hydroxy-4-(3-trifluoromethyl-phenyl)-butyl]-1-[6-(2H-tetrazol-5-yl)-hexyl]-pyrrolidin-2-one

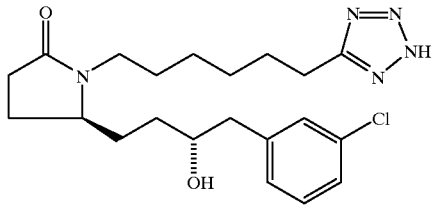

Step A: 7-{2-Oxo-5R-[3-oxo-4-(3-trifluoromethyl-phenyl)-but-1-enyl]-pyrrolidin-1-yl}-heptanenitrile Following the procedure described for Example 1, Step A, the anion derived from [2-oxo-3-(3-trifluoromethyl-phenyl)-propyl]-phosphonic acid dimethyl ester (2.68 g, 8.64 mmol) and NaH (60% in oil, 400 mg, 10 mmol) was reacted with 7-(2R-formyl-5-oxo-pyrrolidin-1-yl)-heptanenitrile (assumed 10 mmol) over 18 h. Purification by medium pressure chromatography (30% EtOAc in hexanes to 80% EtOAc in hexanes) provided 7-{2-oxo-5R-[3-oxo-4-(3-trifluoromethyl-phenyl)-but-1-enyl]-pyrrolidin-1-yl}-heptanenitrile (1.2 g). $^1$H NMR (CDCl$_3$) δ7.52 (m, 1H), 7.45 (m, 2H), 7.37 (m, 1H), 6.67 (dd, 1H), 6.23 (d, 1H), 4.18 (m, 1H), 3.90 (s, 2H), 3.53 (m, 1H), 2.73 (m, 1H), 2.45–2.23 (m, 5H), 1.79 (m, 1H), 1.60 (m, 2H), 1.41 (m, 4H), 1.24 (m, 2H); MS 407.2 (M+1), 405.3 (M−1).

Step B: 7-{2R-[3S-Hydroxy-4-(3-trifluoromethyl-phenyl)-but-1-enyl]-5-oxo-pyrrolidin-1-yl}-heptanenitrile To a solution of 7-{2-oxo-5R-[3-oxo-4-(3-trifluoromethyl-phenyl)-but-1-enyl]-pyrrolidin-1-yl}-heptanenitrile (1.14 g, 2.81 mmol) and (R)-2-methyl-CBS-oxazaborolidine (1M in toluene, 0.42 mL, 0.42 mmol) in CH$_2$Cl$_2$ (112 mL) at −45° C. was added catecholborane (1M in THF, 8.4 mL, 8.4 mmol) dropwise. The reaction mixture was stirred at −45° C. for 18 h and 1N HCl was added. The reaction mixture was stirred at room temperature for 40 minutes and the layers were separated. The organic solution was washed with cold 1N NaOH (3 times). The organic solution was washed sequentially with 1N HCl, water and brine. The organic solution was dried (MgSO$_4$), filtered and concentrated. Purification by medium pressure chromatography (1:1 hexanes:EtOAc to 80% EtOAc in hexanes) provided 7-{2R-[3S-hydroxy-4-(3-trifluoromethyl-phenyl)-but-1-enyl]-5 -oxo-pyrrolidin-1-yl}-heptanenitrile (820 mg) as an approximate 2.5:1 ratio of 3S:3R alcohol diastereomers by $^1$H NMR. $^1$H NMR (CDCl$_3$) δ7.51–7.38 (m, 4H), 5.72 (dd, 1H), 5.49 (dd, 1H), 4.45 (m, 1H), 4.02 (m, 1H), 3.47 (m, 1H), 2.90 (m, 2H), 2.71 (m, 1H), 2.34 (m, 4H), 2.18 (m, 1H), 1.66 (m, 4H), 1.44 (m, 4H), 1.27 (m, 2H); MS 409.2 (M+1).

Step C: 7-{2S-[3R-Hydroxy-4-(3-trifluoromethyl-phenyl)-butyl]-5-oxo-pyrrolidin-1-yl }-heptanenitrile Following the procedure described for Example 1, Step C, 7-{2R-[3S-hydroxy-4-(3-trifluoromethyl-phenyl)-but-1-enyl]-5-oxo-pyrrolidin-1-yl}-heptanenitrile (810 mg) in MeOH (40 mL) was hydrogenated in the presence of 10% palladium on carbon (100 mg) at 50 psi for 18 h on a Parr shaker. Purification by medium pressure chromatography (1:1 hexanes:EtOAc to EtOAc to 3% MeOH in CH$_2$Cl$_2$) provided 7-{2S-[3R-hydroxy-4-(3-trifluoromethyl-phenyl)-butyl]-5-oxo-pyrrolidin-1-yl}-heptanenitrile (720 mg). $^1$H NMR (CDCl$_3$) 67 7.44 (m, 4H), 3.84 (m, 1H), 3.58 (m, 2H), 2.88 (m, 2H), 2.73 (m, 1H), 2.32 (m, 4H), 2.11 (m, 1H), 1.78 (1H), 1.65–1.37 (m, 11H), 1.30 (m, 2H); MS 411.2 (M+1).
Step D: 5S-[3R-Hydroxy-4-(3-trifluoromethyl-phenyl)-butyl]-1-[6-(2H-tetrazol-5-yl)-hexyl]-pyrrolidin-2-one Following the procedure described for Example 3, Step D, 7-{2S-[3R-hydroxy-4-(3-trifluoromethyl-phenyl)-butyl]-5-oxo-pyrrolidin-1-yl }-heptanenitrile (710 mg, 1.73 mmol) was reacted with azidotrimethylsilane (399 mg, 3.46 mmol) and dibutyltin oxide (43 mg, 1.7 mmol) in toluene (25 mL) heated under reflux for 18 h. The volatiles were removed in vacuo and the residue was diluted with $CH_2Cl_2$. The organic solution was washed consecutively with 1N HCl (2 times), water (1 time) and brine (1 time). The organic solution was dried ($MgSO_4$), filtered, and concentrated. The residue was purified by medium pressure chromatography eluting with EtOAc to 2% MeOH in $CH_2Cl_2$ to 8% MeOH in $CH_2Cl_2$ to provide 5S-[3R-hydroxy-4-(3-trifluoromethyl-phenyl)-butyl]-1-[6-(2H-tetrazol-5-yl)-hexyl]-pyrrolidin-2-one (450 mg). $^1$H NMR ($CDCl_3$) δ7.44 (m, 4H), 3.87 (m, 1H), 3.65 (m, 1H), 3.50 (m, 1H), 3.01–2.73 (m, 5H), 2.42 (m, 2H), 2.16 (m, 1H), 1.86–1.23 (m, 14H); MS 454.4 (M+1), 452.4 (M−1).
Step E: Sodium salt of 5S-[3R-Hydroxy-4-(3-trifluoromethyl-phenyl)-butyl]-1-[6-(2H-tetrazol-5-yl)-hexyl]-pyrrolidin-2-one Following the procedure described for Example 2, Step E, treatment of 5S-[3R-hydroxy-4-(3-trifluoromethyl-phenyl)-butyl ]-1-[6-(2H-tetrazol-5-yl)-hexyl]-pyrrolidin-2-one (428 mg, 0.944 mmol) with $NaHCO_3$ (79 mg, 0.94 mmol) provided the sodium salt (430 mg). $^1$H NMR ($CD_3OD$) δ7.48 (m, 4H), 3.79 (m, 1H), 3.67 (m, 1H), 3.51 (m, 1H), 2.86 (m, 5H), 2.30 (m, 2H) 2.12 (m, 1H), 1.84–1.27 (m, 14H); MS 454.4 (M−Na+1), 452.4 (M−Na−1).

EXAMPLE 5

5-[4-(4-Fluoro-phenyl)-3-hydroxy-butyl]-1-[6-(2H-tetrazol-5-yl)-hexyl ]-pyrrolidin-2-one

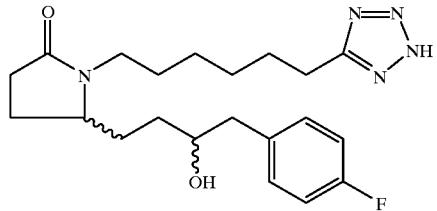

Step A: 7-{2-[3-(tert-Butyl-dimethyl-silanyloxy)-4-(4-fluoro-phenyl)-butyl]-5-oxo-pyrrolidin-1-yl}-heptanenitrile A solution o f 5-[3-(tert-butyl-dimethyl-silanyloxy)4-(4-fluoro-phenyl)-butyl]-pyrrolidin-2-one (150 mg, 0.41 mmol) in DMF (5 mL) was added to NaH (60% by weight in oil, 16 mg, 0.41 mmol) in DMF (10 mL). After 1.5 h, 7-bromoheptanenitrile (78 mg, 0.41 mmol) in DMF (5 mL) was added and the reaction mixture was stirred at 90° C. for 2.5 h. Water (20 mL) was added and the aqueous solution was washed with EtOAc (4×15 mL). The combined organic solutions were washed with water (2×15 mL), dried ($MgSO_4$), filtered, and concentrated. The residue was purified by medium pressure chromatography (1:1 hexanes:EtOAc) provided 7-{2-[3-(tert-butyl-dimethyl-silanyloxy)-4-(4-fluoro-phenyl)-butyl ]-5-oxo-pyrrolidin-1-yl}-heptanenitrile (161 mg). $^1$H NMR ($CDCl_3$) δ7.09 (m, 2H), 6.95 (m, 2H), 3.81 (m, 1H), 3.54 (m, 2H), 2.86 (m, 1H), 2.68 (m, 2H), 2.29 (m, 4H), 2.06 (m, 1H), 1.74–1.23 (m, 13H), 0.85 (s, 9H), 0.04 (m, 3H), 0.19 (m, 3H); MS 475.1 (M+1).

Step B: 7-{2-[4-(4-Fluoro-phenyl)-3-hydroxy-butyl]-5-oxo-pyrrolidin-1-yl }-heptanenitrile To a solution of 7-{2-[3-(tert-butyl-dimethyl-silanyloxy)-4-(4-fluoro-phenyl)-butyl]-5-oxo-pyrrolidin-1-yl}-heptanenitrile (158 mg, 0.333 mmol) in THF (20 mL) at 0° C. was added TBAF (1M in THF, 0.50 mL, 0.50 mmol). The reaction mixture was stirred at room temperature for 3 h and saturated aqueous $NaHCO_3$ was added. The volatiles were removed in vacuo. The remaining aqueous solution was washed with $CHCl_3$ (4×5 mL) and the combined organic solutions were dried ($MgSO_4$), filtered and concentrated. The residue was purified by medium pressure chromatography (1:1 hexanes:EtOAc to EtOAc) provided 7-{2-[4-(4-fluoro-phenyl)-3-hydroxy-butyl]-5-oxo-pyrrolidin-1-yl}-heptanenitrile (82 mg). $^1$H NMR ($CDCl_3$) δ7.15 (m, 2H), 7.00 (m, 2H), 3.77 (m, 1H), 3.58 (m, 2H), 2.89 (m, 1H), 2.79 (m, 1H), 2.64 (m, 1H), 2.34 (m, 4H), 2.12 (m, 1H), 1.68–1.24 (m, 14H); MS 361.2 (M+1).

Step C: 5-[4-(4-Fluoro-phenyl)-3-hydroxy-butyl]-1-[6-(2H-tetrazol-5-yl)-hexyl ]-pyrrolidin-2-one Following the procedure described for Example 3, Step D, 7-{2-[4-(4-fluoro-phenyl)-3-hydroxy-butyl]-5-oxo-pyrrolidin-1-yl}-heptanenitrile (71 mg, 0.197 mmol) was reacted with azidotrimethylsilane (45 mg, 0.394 mmol) and dibutyltin oxide (5 mg, 0.02 mmol) in toluene (10 mL) heated under reflux for 16 h. Additional azidotrimethylsilane (200 mg) and dibutyltin oxide (50 mg) were added and the reaction mixture was heated under reflux for 5 h. The reaction mixture was acidified with 1N HCl to pH=2 (5 mL) and the aqueous solution was washed with EtOAc (4×10 mL). The combined organic solutions were dried ($MgSO_4$), filtered, and concentrated. Purification by medium pressure chromatography (EtOAc to 39:1 EtOAc:MeOH to 19:1 EtOAc:MeOH) provided the title compound of Example 5A (39 mg). $^1$H NMR ($CDCl_3$) 67 7.16 (m, 2H), 7.00 (m, 2H), 3.81 (m, 1H), 3.68 (m,1H), 3.53 (m, 1H), 2.99 (m, 3H), 2.80 (m, 1H), 2.68 (m, 1H), 2.47 (m, 2H), 2.20 (m, 1H), 1.88–1.22 (m, 14H); MS 404.3 (M+1); 402.3 (M−1).

EXAMPLE 6

5-(4-Biphenyl-3-yl-3-hydroxy-butyl)-1-[6-(2H-tetrazol-5-yl)-hexyl]-pyrrolidin-2-one

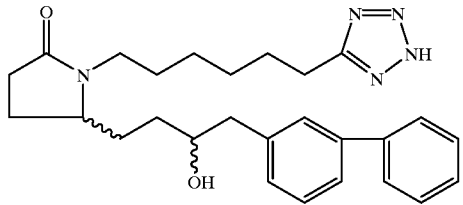

Step A: 7-{2-[4-Biphenyl-3-yl-3-(tert-butyl-dimethyl-silanyloxy)-butyl]-5-oxo-pyrrolidin-1-yl}-heptanenitrile Following the procedure described for Example 5, Step A, the anion derived from 5-[4-biphenyl-3-yl-3-(tert-butyl-dimethyl-silanyloxy)-butyl]-pyrrolidin-2-one (239.1 mg, 0.564 mmol) and NaHMDS (1M in THF, 0.67 mL, 0.67 mmol) was alkylated with 7-bromoheptanenitrile (118 mg, 0.620 mmol) at 70° C. for 24 h. Purification by medium pressure chromatography ($CH_2Cl_2$ to 1% MeOH in $CH_2Cl_2$ to 2% MeOH in $CH_2Cl_2$ to 4% MeOH in $CH_2Cl_2$) provided 7-{2-[4yl-3-(tert-butyl-dimethyl-silanyloxy)-butyl]-5-oxo-pyrrolidin-1-yl}-heptanenitrile (187 mg). MS 533.3 (M+1).
Step B: 7-[2-(4-Biphenyl-3-yl-3-hydroxy-butyl)-5-oxo-pyrrolidin-1-yl]-heptanenitrile Following the procedure described for Example 5, Step B, 7-{2-[4-biphenyl-3-yl-3-(tert-butyl-dimethyl-silanyloxy)-butyl]-5-oxo-pyrrolidin-1-yl}-heptanenitrile (187 mg, 0.351 mmol) was deprotected with TBAF (1M in THF, 0.53 mL, 0.53 mmol). The addition was performed at 0° C. and the reaction mixture was stirred at room temperature for 24 h. Purification by medium pressure chromatography (CH$_2$Cl$_2$ to 1% MeOH in CH$_2$Cl$_2$ to 2% MeOH in CH$_2$Cl$_2$ to 6% MeOH in CH$_2$Cl$_2$ to 10% MeOH in CH$_2$Cl$_2$) provided 7-[2-(4-biphenyl-3-yl-3-hydroxy-butyl)-5-oxo-pyrrolidin-1-yl]-heptanenitrile (85 mg). $^1$H NMR (CDCl$_3$) δ7.58 (m, 1H), 7.51–7.33 (m, 4H), 7.21–7.12 (m, 4H), 3.85 (m, 1H), 3.60 (m, 2H), 2.90 (m, 1H), 2.83–2.60 (m, 2H), 2.45–2.30 (m, 4H), 2.14 (m, 1H), 1.73–1.25 (m, 14H).

Step C: 5-(4-Biphenyl-3-yl-3-hydroxy-butyl)-1-[6-(2H-tetrazol-5-yl)-hexyl]-pyrrolidin-2-one Following the procedure described for Example 3, Step D, 7-[2-(4-biphenyl-3-yl-3-hydroxy-butyl)-5-oxo-pyrrolidin-1-yl]-heptanenitrile (109 mg, 0.260 mmol) was reacted with azidotrimethylsilane (0.69 mL, 0.52 mmol) and dibutyltin oxide (11 mg, 0.044 mmol) in toluene (5.3 mL) heated at reflux for 72 h. The reaction mixture was cooled and water was added. The mixture was acidified with 1N HCl to pH=2 and the aqueous solution was washed with 5% MeOH in CH$_2$Cl$_2$ (3 times). The combined organic solutions were dried (MgSO$_4$), filtered, and concentrated. Purification by medium pressure chromatography (1:1 hexanes:EtOAc to EtOAc to 2% MeOH in CH$_2$Cl$_2$ to 4% MeOH in CH$_2$Cl$_2$ to 8% MeOH in CH$_2$Cl$_2$) provided the title compound of Example 6(107 mg). $^1$H NMR (CDCl$_3$) δ7.57 (m, 1H), 7.51–7.32 (m, 4H), 7.25–7.13 (m, 4H), 3.91 (m, 1H), 3.74–3.50 (m, 2H), 2.96 (m, 3H), 2.77 (m, 1H), 2.50(m, 2H), 2.22 (m, 1H), 2.07 (m, 1H), 1.90–1.22 (m, 14H); MS 462.2 (M+1), 460.1 (M−1).

EXAMPLE 7

5-[4-(3-Fluoro-phenyl)-3-hydroxy-butyl]-1-[6-(2H-tetrazol-5-yl)-hexyl]-pyrrolidin-2-one

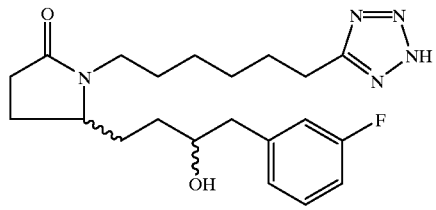

Step A: 7-{2-[3-(tert-Butyl-dimethyl-silanyloxy)-4-(3-fluoro-phenyl)-butyl]-5-oxo-pyrrolidin-1-yl}-heptanenitrile Following the procedure described for Example 5, Step A, the anion derived 5-[3-(tert-butyl-dimethyl-silanyloxy)-4-(3-fluoro-phenyl)-butyl]-pyrrolidin-2-one (250 mg, 0.684 mmol) and NaHMDS (1M in THF, 0.80 mL, 0.80 mmol) was alkylated with 7-bromoheptanenitrile (142 mg, 0.748 mmol) at 70° C. for 72 h. Purification by medium pressure chromatography (1:1 hexanes:EtOAc to EtOAc to 5% MeOH in CH$_2$Cl$_2$) provided 7-{2-[3-(tert-butyl-dimethyl-silanyloxy)-4-(3-fluoro-phenyl)-butyl]-5-oxo-pyrrolidin-1-yl}-heptanenitrile (261.7 mg). $^1$H NMR (CDCl$_3$) δ7.26 (m, 1H), 6.92 (m, 3H), 3.89 (m, 1H), 3.59 (m, 2H), 2.89 (m, 1H), 2.75 (m, 2H), 2.36 (m, 4H), 2.11 (m, 1H), 1.72–1.26 (m, 13H), 0.89 (s, 9H), 0.09 (s, 6H); MS 475.3 (M+1).

Step B: 7-{2-[4-(3-Fluoro-phenyl)-3-hydroxy-butyl]-5-oxo-pyrrolidin-1-yl}-heptanenitrile Following the procedure described for Example 5, Step B, 7-{2-[3-(tert-butyl-dimethyl-silanyloxy)-4-(3-fluoro-phenyl)-butyl]-5-oxo-pyrrolidin-1-yl}-heptanenitrile (261.7 mg, 0.551 mmol) was deprotected with TBAF (1M in THF, 0.83 mL, 0.83 mmol). The addition was performed at 0° C. and the reaction mixture was stirred at room temperature for 24 h. Purification by medium pressure chromatography (CH$_2$Cl$_2$ to 1% MeOH in CH$_2$Cl$_2$ to 2% MeOH in CH$_2$Cl$_2$ to 4% MeOH in CH$_2$Cl$_2$) provided 7-{2-[4-(3-fluoro-phenyl)-3-hydroxy-butyl]-5-oxo-pyrrolidin-1-yl}-heptanenitrile (141 mg). $^1$H NMR (CDCl$_3$) δ7.32 (m, 1H), 6.98 (m, 3H), 3.86 (m, 1H), 3.64 (m, 2H), 2.99–2.80 (m, 2H), 2.71 (m, 1H), 2.38 (m, 4H), 2.16 (m, 1H), 1.74–1.29 (m, 14H); MS 361.3 (M+1).

Step C: 5-[4-(3-Fluoro-phenyl)-3-hydroxy-butyl]-1-[6-(2H-tetrazol-5-yl)-hexyl]-pyrrolidin-2-one Following the procedure described for Example 6, Step C, 7-{2-[4-(3-fluoro-phenyl)-3-hydroxy-butyl]-5-oxo-pyrrolidin-1-yl}-heptanenitrile (141.3 mg, 0.392 mmol) was reacted with azidotrimethylsilane (0.210 mL, 1.57 mmol) and dibutyltin oxide (29 mg, 0.116 mmol) in toluene (8 mL) heated under reflux for 72 h. Purification by medium pressure chromatography (CH$_2$Cl$_2$ to 2% MeOH in CH$_2$Cl$_2$ to 4% MeOH in CH$_2$Cl$_2$ to 6% MeOH in CH$_2$Cl$_2$) provided the title compound of Example 5C (101.5 mg). $^1$H NMR (CDCl$_3$) δ7.26 (m, 1H), 6.94 (m, 3H), 3.87 (m, 1H), 3.70 (m, 1H), 3.52 (m, 1H), 2.98 (m, 3H), 2.78 (m, 2H), 2.48 (m, 2H), 2.20 (m, 1H), 1.89–1.24 (m, 14H); MS 404.2 (M+1), 401.9 (M−1).

EXAMPLE 8

5S[4-(3-Chloro-phenyl)-3R-hydroxy-butyl]-1-[6-(2H-tetrazol-5-yl)-hexyl]-pyrrolidin-2-one

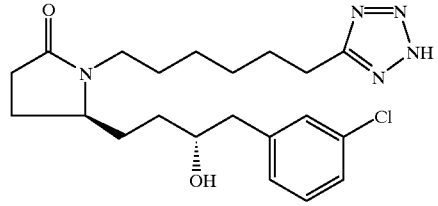

Step A: 7-{2R-[3S-hydroxy-4-(3-chloro-phenyl)-but-1-enyl]-5-oxo-pyrrolidin-1-yl}-heptanenitrile To a solution of 7-{2-oxo-5R-[3-oxo-4-(3-chloro-phenyl)-but-1-enyl]-pyrrolidin-1-yl}-heptanenitrile (1.62 g, 4.34 mmol) in CH$_2$Cl$_2$ (200 mL) at −45° C. was added (R)-2-methyl-CBS-oxazaborolidine (1M in toluene, 1.3 mL, 1.3 mmol). After stirring for 20 minutes, catecholborane (1M in THF, 13 mL, 13 mmol) was added dropwise. The reaction was stirred at −45° C. for 16 h and 1N HCl was added. The mixture was warmed to room temperature and the layers were separated. The organic solution was washed with cold 1N NaOH (3 times). The organic solution was washed sequentially with 1N HCl, water, and brine. The organic solution was dried (MgSO$_4$), filtered, and concentrated. Purification by medium pressure chromatography (1:1 hexanes:EtOAc to 20% MeOH in CH$_2$Cl$_2$) provided 7-{2R-[3S-hydroxy-4-(3-chloro-phenyl)-but-1-enyl]-5-oxo-pyrrolidin-1-yl}-heptanenitrile (536 mg) as an 8.2:1 mixture of 3S:2R alcohol by HPLC. $^1$H NMR (CDCl$_3$) δ7.24–7.17 (m, 3H), 7.07 (m, 1H), 5.69 (dd, 1H), 5.46 (dd, 1H), 4.40 (m, 1H), 4.01 (m, 1H), 3.46 (m, 1H) 2.81 (m, 2H), 2.68 (m, 1H), 2.42–2.28 (m, 4H), 2.20 (m, 1H), 1.73–1.59 (m, 4H), 1.42 (m, 4H), 1.25 (m, 2H); MS 375 (M+1).

Step B: 7-{2S-[4-(3-chloro-phenyl)-3R-hydroxy-butyl]-5-oxo-pyrrolidin-1-yl}-heptanenitrile Following the procedure described for Example 4, Step C, 7-{2R-[3S-hydroxy-4-(3-chloro-phenyl)-but-1-enyl]-5-oxo-pyrrolidin-1-yl}-heptanenitrile (536 mg) in EtOH (30 mL) was hydrogenated in the presence of 10% palladium on carbon (60 mg) for 3.5 h. Purification by medium pressure chromatography (1:1 hexanes:EtOAc to 20% MeOH in $CH_2Cl_2$ provided 7-{2S-[4-(3-chloro-phenyl)-3R-hydroxy-butyl]-5-oxo-pyrrolidin-1-yl}-heptanenitrile (440 mg). $^1$H NMR ($CDCl_3$) δ7.22 (m, 3H), 7.08 (m, 1H), 3.83 (m, 1H), 3.59 (m, 2H), 2.90 (m, 1H), 2.77 (dd, 1H), 2.66 (dd, 1H), 2.39–2.29 (m, 4H), 2.11 (m, 1H), 1.78 (m, 1H), 1.68–1.39 (m, 11H), 1.29 (m, 2H); MS 377.2 (M+1).

Step C: S-[4-(3-Chloro-phenyl)-3R-hydroxy-butyl]-1-[6-(2H-tetrazol-5-yl)-hexyl ]-pyrrolidin-2-one Following the procedure described for Example 3, Step D, a mixture of 7-{2S-[4-(3-chloro-phenyl)-3R-hydroxy-butyl]-5-oxo-pyrrolidin-1-yl }-heptanenitrile (420 mg, 1.114 mmol), trimethylsilylazide (257 mg, 2.23 mmol), and dibutyltin oxide (56 mg) in toluene (30 mL) was heated at reflux for 16 h. The volatiles were removed in vacuo and the residue was dissolved in MeOH and stirred with 3N HCl for 3 h. The reaction was diluted with water and $CH_2Cl_2$ and the layers were separated. The organic layer was washed with water followed by brine. The organic solution was dried ($MgSO_4$), filtered, and concentrated. Purification by medium pressure chromatography (EtOAc to 2% MeOH in $CH_2Cl_2$ to 7% MeOH in $CH_2Cl_2$) provided 5S-[4-(3-chloro-phenyl)-3R-hydroxy-butyl]-1-[6-(2H-tetrazol-5-yl)-hexyl]-pyrrolidin-2-one (311 mg). $^1$H NMR ($CDCl_3$) δ7.22 (m, 3H), 7.08 (m, 1H), 3.86 (m, 1H), 3.66 (m, 1H), 3.52 (m, 1H), 2.96 (m, 3H), 2.82–2.68 (m, 2H), 2.45 (m, 2H), 2.17 (m, 1H), 1.88–1.22 (m, 14H); MS 420.2 (M+1), 418.3 (M−1).

EXAMPLE 9

7-{2R-[3-Hydroxy-4-(3-phenoxy-phenyl)-but-1-enyl]-5-oxo-pyrrolidin-1-yl }-heptanoic acid

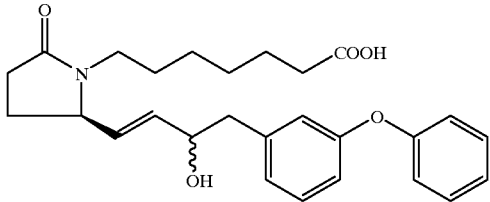

Step A: 7-{2-Oxo-5R-[3-oxo-4-(3-phenoxy-phenyl)-but-1-enyl]-pyrrolidin-1-yl}-heptanoic acid ethyl ester Following the procedure described for Example 1, Step A, the anion derived from [2-oxo-3-(3-phenoxy-phenyl)-propyl]-phosphonic acid dimethyl ester (633 mg, 1.98 mmol) and NaH (60% in oil, 70 mg, 1.74 mmol) was reacted with 7-(2R-formyl-5-oxo-pyrrolidin-1-yl)-heptanoic acid ethyl ester (assumed 1.58 mmol) over 24 h. Medium pressure chromatography (EtOAc) provided 7-{2-oxo-5R[3-oxo-4-(3-phenoxy-phenyl)-but-1-enyl]-pyrrolidin-1-yl}-heptanoic acid ethyl ester (215 mg). $^1$H NMR ($CDCl_3$) δ7.28 (m, 3H), 7.08 (m, 1H), 6.97 (m, 2H), 6.89 (m, 2H), 6.83 (m, 1H), 6.62 (dd, 1H), 6.19 (d, 1H), 4.13 (m, 1H), 4.08 (q, 2H), 3.79 (s, 2H), 3.51 (m, 1H), 2.68 (m, 1H), 2.35 (m, 2H), 2.24 (m, 3H), 2.24 (m, 3H), 1.75 (m, 1H), 1.54 (m, 2H), 1.43–1.20 (m, 9H).

Step B: 7-{2R-[3-hydroxy-4-(3-phenoxy-phenyl)-but-1-enyl]-5-oxo-pyrrolidin-1-yl }-heptanoic acid ethyl ester Following the procedure described for Example 3, Step C, 7-{2-oxo-5R-[3-oxo-4-(3-phenoxy-phenyl)-but-1-enyl]-pyrrolidin-1-yl}-heptanoic acid ethyl ester (215 mg, 0.451 mmol) was reacted with $NaBH_4$ (17 mg, 0.45 mmol) in EtOH (3 mL) at 0° C. over 4 h. Purification by medium pressure chromatography (EtOAc) provided 7-{2R-[3-hydroxy-4-(3-phenoxy-phenyl)-but-1-enyl]-5-oxo-pyrrolidin-1-yl }-heptanoic acid ethyl ester (167 mg). $^1$H NMR ($CDCl_3$) δ7.33 (m, 2H), 7.25 (m, 1H), 7.10 (m, 1H), 6.99 (m, 2H), 6.93 (m, 1H), 6.86 (m, 2H), 5.72 (m, 1H), 5.45 (m, 1H), 4.37 (m, 1H), 4.10 (q, 2H), 3.47 (m, 1H), 2.82 (m, 3H), 2.35 (m, 2H), 2.26 (t, 2H), 2.15 (m, 1H), 1.70–1.21 (m, 13H).

Step C: 7-{2R-[3-Hydroxy-4-(3-phenoxy-phenyl)-but-1-enyl]-5-oxo-pyrrolidin-1 -yl}-heptanoic acid Following the procedure described for Example 1, Step D, 7-{2R-[3-hydroxy-4-(3-phenoxy-phenyl)-but-1-enyl]-5-oxo-pyrrolidin-1-yl}-heptanoic acid ethyl ester (29 mg, 0.060 mmol) was hydrolyzed with 2M NaOH in EtOH (4.0 mL) at room temperature over 24 h to provide the title compound (20 mg). $^1$H NMR ($CDCl_3$) δ7.33–7.21 (m, 3H), 7.08 (m, 1H), 6.98–6.84 (m, 5H), 5.70 (m, 1H), 5.44 (m, 1H), 4.36 (m, 1H), 4.00 (m, 1H), 3.44 (m, 1H), 2.85–2.51 (m, 3H), 2.32 (m, 4H), 2.14 (m, 1H), 1.68–1.18 (m, 10H).

EXAMPLE 10

7-{2S-[3-Hydroxy-4-(3-phenoxy-phenyl)-butyl]-5-oxo-pyrrolidin-1-yl}-heptanoic acid

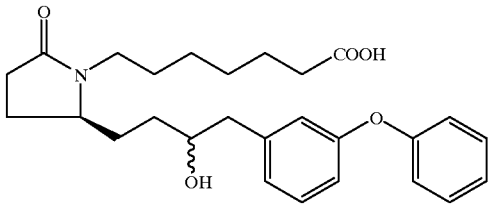

Step A: 7-{2S-[3-Hydroxy-4-(3-phenoxy-phenyl)-butyl]-5-oxo-pyrrolidin-1-yl}-heptanoic acid ethyl ester Following the procedure described for Example 1, Step C, a mixture of 7-{2R-[3-hydroxy-4-(3-phenoxy-phenyl)-but-1-enyl]-5-oxo-pyrrolidin-1-yl}-heptanoic acid ethyl ester (139 mg, 0.290 mmol), MeOH (30 mL), and 10% palladium on carbon (14 mg) was hydrogenated on a Parr shaker at 50 psi for 18 h. Purification by medium pressure chromatography (1:1 hexanes:EtOAc) provided 7-{2S-[3-hydroxy-4-(3-phenoxy-phenyl)-butyl]-5-oxo-pyrrolidin-1-yl}-heptanoic acid ethyl ester (86 mg). $^1$H NMR ($CDCl_3$) δ7.35–7.24 (m, 3H), 7.10 (m, 1H), 6.99 (m, 2H), 6.93 (m, 1H), 6.8 (m, 2H), 4.09 (q, 2H), 3.80 (m, 1H), 3.58 (m, 2H), 2.82 (m, 2H), 2.64 (m, 1H), 2.42–2.24 (m, 4H), 2.10 (m, 1H), 1.77 (m, 1H), 1.66–1.21 (m, 16H).

Step B: 7-{2S-[3-Hydroxy-4-(3-phenoxy-phenyl)-butyl]-5-oxo-pyrrolidin-1-yl}-heptanoic acid Following the procedure described for Example 1, Step D, 7-{2S-[3-hydroxy-4-(3-phenoxy-phenyl)-butyl]-5-oxo-pyrrolidin-1-yl}-heptanoic acid ethyl ester (86 mg, 1.79 mmol) was hydrolyzed with 2N NaOH in MeOH (4 mL) over 18 h to provide the title compound (62 mg). $^1$H NMR ($CDCl_3$) δ7.33–7.23 (m, 3H), 7.09 (m, 1H), 6.98 (m, 2H), 6.91 (m, 1H), 6.86 (m, 2H), 3.80 (m, 1H), 3.56 (m, 2H), 2.88 (m, 1H), 2.77 (m, 1H) 2.64 (m, 1H), 2.38–2.28 (m, 4H), 2.09 (m, 1H), 1.77 (m, 1H), 1.64–1.21 (m, 13H).

Preparation 1

7-(2R-Hydroxymethyl-5-oxo-pyrrolidin-1-yl)-heptanenitrile

Step A: 7-[2R-(tert-Butyl-dimethyl-silanyloxymethyl)-5-oxo-pyrrolidin-1-yl]-heptanenitrile To a mixture of NaH (60% in oil, 3.836 g, 0.0959 mmol, washed with 25 mL DMF) in DMF (250 mL) was added a solution of 5R-(tert-butyl-dimethyl-silanyloxymethyl)-pyrrolidin-2-one (Tetrahdedron: Asymmetry, 1996, 7, 2113) (20.00 g, 87.19 mmol) in DMF (50 mL). The reaction was stirred at room temperature for 1.5 h and a solution of 7-bromoheptanonitrile (16.574 g, 87.19 mmol) in DMF (50 mL) was added. The reaction was stirred at 90° C. for 3 h. The reaction was cooled to room temperature and water (750 mL) was added. The aqueous solution was washed with EtOAc (4×250 mL). The combined organic solutions were washed with water (2×250 mL), dried (MgSO$_4$), filtered, and concentrated. Purification by medium pressure chromatography eluting with a solvent gradient (9:1 hexanes:EtOAc to 7:3 hexanes:EtOAc to 1:1 hexanes:EtOAc) provided 7-[2R-(tert-butyl-dimethyl-silanyloxymethyl)-5-oxo-pyrrolidin-1-yl]-heptanenitrile (22.46 g). $^1$H NMR (CDCl$_3$) δ3.69–3.55 (m, 4H), 2.99 (m, 1H), 2.42 (m, 1H), 2.34–2.24 (m, 3H), 2.05 (m, 1H), 1.81 (m, 1H), 1.67–1.42 (m, 6H), 1.31 (m, 2H), 0.86 (s, 9H), 0.03 (s, 6H); MS 339.3 (M+1).

Step B: 7-(2R-Hydroxymethyl-5-oxo-pyrrolidin-1-yl)-heptanenitrile

A solution of tetrabutylammonium fluoride (1M in THF, 100.0 mL, 100.0 mmol) was slowly added to a solution of 7-[2R-(tert-butyl-dimethyl-silanyloxymethyl)-5-oxo-pyrrolidin-1-yl]-heptanenitrile (22.39 g, 66.13 mmol) in THF (400 mL) at 0° C. The reaction was warmed to room temperature and was stirred for 4 h. Saturated aqueous NaHCO$_3$ (250 mL) was added and the volatiles were removed in vacuo. The remaining aqueous solution was washed with CHCl$_3$ (4×200 mL). The combined organic solutions were dried (MgSO$_4$), filtered, and concentrated. Purification by medium pressure chromatography eluting with a solvent gradient (9:1 hexanes:EtOAc to 4:1 hexanes:EtOAc to 7:3 hexanes:EtOAc to 6:4 hexanes:EtOAc to 1:1 hexanes:EtOAc to EtOAc to 9:1 EtOAc:MeOH) provided 7-(2R-hydroxymethyl-5-oxo-pyrrolidin-1-yl)-heptanenitrile (14.922 g). $^1$H NMR (CDCl$_3$) δ3.78 (dd, 1H), 3.71–3.58 (m, 3H), 3.00 (m, 1H), 2.46 (m, 1H), 2.36–2.27 (m, 3H), 2.08 (m, 1H), 1.93 (m, 1H), 1.77 (m, 1H), 1.68–1.43 (m, 6H), 1.32 (m, 2H); MS 225.1 (M+1).

Preparation 2

7-(2R-Hydroxymethyl-5-oxo-pyrrolidin-1-yl)-heptanoic acid ethyl ester

Step A: 7-[2R-(tert-Butyl-dimethyl-silanyloxymethyl)-5-oxo-pyrrolidin-1-yl]-heptanoic acid ethyl ester Following the procedure described for Preparation 1, Step A, the anion derived from 5R-(tert-butyl-dimethyl-silanyloxymethyl)-pyrrolidin-2-one (30.000 g, 130.8 mmol) and NaH (60% in oil, 5.756 g, 143.9 mmol) in DMF (600 mL) was reacted with ethyl 7-bromoheptanoate (32.559 g, 137.3 mmol) for 3 h at 90° C. Purification by medium pressure chromatography eluting with a solvent gradient (9:1 hexanes:EtOAc to 4:1 hexanes:EtOAc to 7:3 hexanes:EtOAc to 6:4 hexanes:EtOAc) provided 7-[2R-(tert-butyl-dimethyl-silanyloxymethyl)-5-oxo-pyrrolidin-1-yl]-heptanoic acid ethyl ester (39.46 g). $^1$H NMR (CDCl$_3$) δ4.10 (q, 2H), 3.62 (m, 4H), 2.95 (m, 1H), 2.42 (m, 1H), 2.27 (m, 3H), 2.04 (m, 1H), 1.81 (m, 1H), 1.65–1.26 (m, 8H), 1.23 (t, 3H), 0.86 (s, 9H), 0.03 (s, 6H); MS 386.2 (M+1).

Step B: 7-(2R-Hydroxymethyl-5-oxo-pyrrolidin-1-yl)-heptanoic acid ethyl ester

Following the procedure described for Preparation 1, Step B, 7-[2R-(tert-butyl-dimethyl-silanyloxymethyl)-5-oxo-pyrrolidin-1-yl]-heptanoic acid ethyl ester (39.46 g, 102.3 mmol) was deprotected with TBAF (1M in THF, 154.0 mL, 154.0 mmol) with a reaction time of 2.5 h. Purification by medium pressure chromatography eluting with a solvent gradient (9:1 hexanes:EtOAc to 6:4 hexanes:EtOAc to 1:1 hexanes:EtOAc to EtOAc to 19:1 EtOAc:MeOH) provided 7-(2R-hydroxymethyl-5-oxo-pyrrolidin-1-yl)-heptanoic acid ethyl ester (25.41 g). $^1$H NMR (CDCl$_3$) δ4.10 (q, 2H), 3.77 (dd, 1H), 3.64 (m, 3H), 2.96 (m, 1H), 2.46 (m, 1H), 2.35–2.25 (m, 3H), 2.08 (m, 1H), 1.93 (m, 1H), 1.71 (m, 1H), 1.63–1.27 (m, 8H), 1.23 (t, 3H); MS 272.2 (M+1).

Preparation 3

[2-Oxo-3-(3-trifluoromethyl-phenyl)-propyl]-phosphonic acid dimethyl ester

Step A: N-Methoxy-N-methyl-2-(3-trifluoromethyl-phenyl)-acetamide

To a solution of N,O-dimethylhydroxylamine hydrochloride (1.577 g, 16.2 mmol) in DMF (25 mL) and CH$_2$Cl$_2$ (25 mL) at 0° C. was added triethylamine (2.25 mL). After stirring for 5 minutes, 3-trifluoromethylphenyl acetic acid (3.0 g, 14.7 mmol), HOBT (3.177 g, 23.5 mmol), and DEC (2-diethylaminoethyl chloride hydrochloride, 3.10 g, 16.2 mmol) were added. The reaction mixture was stirred at room temperature for 18 h and was concentrated in vacuo. The residue was diluted with EtOAc and the organic solution was washed consecutively with 1N NaOH (2 times), water, and brine. The organic solution was dried (MgSO$_4$), filtered and concentrated in vacuo. Medium pressure chromatography (20% EtOAc in hexanes to 50% EtOAc in hexanes) provided N-methoxy-N-methyl-2-(3-trifluoromethyl-phenyl)-acetamide.

Step B: [2-Oxo-3-(3-trifluoromethyl-phenyl)-propyl]-phosphonic acid dimethyl ester To a solution of dimethyl methylphosphonate (9.4 g, 75.8 mmol) in toluene (80 mL) at −78° C. was slowly added n-BuLi (2.5M in hexanes, 28 mL, 70 mmol). The reaction mixture was stirred for 1 h and a solution of N-methoxy-N-methyl-2-(3-trifluoromethyl-phenyl)-acetamide (14.39 g) in toluene (50 mL) was slowly added. The reaction mixture was stirred for 2.5 h and AcOH (40 mL) was added. The reaction mixture was warmed to room temperature and water was added. The organic layer was washed with water followed by brine. The organic solution was dried (MgSO$_4$), filtered and concentrated in vacuo. Medium pressure chromatography (CH$_2$Cl$_2$ to 2% MeOH in CH$_2$Cl$_2$) provided the title compound of Preparation 3 (9.37 g). $^1$H NMR (CDCl$_3$) δ7.52 (m, 1H), 7.44 (m, 2H), 7.37 (m, 1H), 3.96 (s, 2H), 3.87 (s, 3H), 3.76 (s, 3H), 3.12 (d, 2H).

Preparation 4

[3-(3-Chloro-phenyl)-2-oxo-propyl]-phosphonic acid dimethyl ester

Substituting the appropriate starting materials, the title compound of Preparation 4 was prepared following an analogous procedure to that described for Preparation 3.

Preparation 5

[3-(3-Chloro-phenyl)-2-oxo-propyl]-phosphonic acid dimethyl ester

To a solution of dimethyl methylphosphonate (17.93 g, 144 mmol) in THF (270 mL) at −78° C. was slowly added n-BuLi (2.5M, 64.2 mL, 160.6 mmol). The reaction mixture was stirred for 1 h and (3-chloro-phenyl)-acetic acid methyl ester (26.93 g, 146 mmol) was slowly added. The reaction mixture was allowed to warm to room temperature and was stirred for 24 h. AcOH (15 mL) was added and the volatiles were removed in vacuo. The residue was diluted with $CH_2Cl_2$ and the organic solution was washed carefully with saturated aqueous $NaHCO_3$ (3 times). The organic layer was dried ($MgSO_4$), filtered and concentrated in vacuo. Purification by medium pressure chromatography (20% EtOAc in hexanes to EtOAc) provided the title compound (9.28 g).

Preparation 6

Tetrahydro-pyrrolizine-3,5-dione

The title compound of Preparation 6 was prepared following the procedure described in U.S. Pat. No. 4,663,464.

Preparation 7

7-(2R-Formyl-5-oxo-pyrrolidin-1-yl)-heptanoic acid ethyl ester

To a solution of 7-(2R-hydroxymethyl-5-oxo-pyrrolidin-1-yl)-heptanoic acid ethyl ester (1.63 g, 6.01 mmol) in benzene (50 mL) was added 1-(3-dimethylaminopropyl)-3-ethylcarbodiimide hydrochloride (3.46 g, 18.03 mmol) and DMSO (1.5 mL, 24.04 mmol). The solution was cooled to 0° C. and pyridinium trifluoroacetate (1.28 g, 6.61 mmol) was added. The reaction mixture was stirred at 0° C. for 15 minutes and then at room temperature for 2 h. The solution was decanted from the oily residue. The residue was washed with benzene (3×) and the combined benzene washes were concentrated in vacuo to provide 7-(2R -formyl-5-oxo-pyrrolidin-1-yl)-heptanoic acid ethyl ester, which was used without further purification.

Preparation 8

4-(3-{2-[4-Biphenyl-3-yl-3-(tert-butyl-dimethyl-silanyloxy)-butyl]-5-oxo-pyrrolidin-1-yl}-propyl)-benzoic acid methyl ester Step A: 5-(3-Bromo-3-oxo-butyl)-pyrrolidin-2-one To a solution of tetrahydro-pyrrolizine-3,5-dione (5 g, 36 mmol) in $CH_2Cl_2$ (320 mL) at 0° C. was added 3-bromobenzylmagnesium bromide (0.25M in $Et_2O$, 155 mL, 38.8 mmol) dropwise. The solution was stirred at 0° C. for 2 h and was quenched with saturated aqueous ammonium chloride. Aqueous 1N HCl was added to achieve a pH=3. After warming to room temperature, the aqueous solution was extracted with $CH_2Cl_2$ (3×). The combined organic extracts were dried ($MgSO_4$), filtered, and concentrated. Purification by medium pressure chromatography using a solvent gradient (1:1 hexanes:EtOAc to EtOAc to 5% MeOH in $CH_2Cl_2$) provided 5-(3-bromo-3-oxo-butyl)-pyrrolidin-2-one (7.84 g). $^1$H NMR ($CDCl_3$) δ7.41–7.11 (m, 4H), 6.24 (bs, 1H), 3.67 (s, 2H), 3.60 (m, 1H), 2.52 (t, 2H), 2.32 (m, 2H), 2.20 (m, 1H), 1.88–1.60 (m, 3H).

Step B: 5-(3-Bromo-3-hydroxy-butyl)-pyrrolidin-2-one

To a solution of 5-(3-bromo-3-oxo-butyl)-pyrrolidin-2-one (7.84 g, 25.3 mmol) in EtOH (130 mL) at 0° C. was added $NaBH_4$ (480 mg, 12.6 mmol) and the reaction was stirred at 0° C. for 2.5 h. The reaction was quenched with saturated aqueous ammonium chloride. Water and $CH_2Cl_2$ were added. The aqueous layer was washed with $CH_2Cl_2$ (3×) and the combined organic extracts were dried ($MgSO_4$), filtered, and concentrated. Purification by medium pressure chromatography using a solvent gradient (1:1 hexanes:E-tOAc to EtOAc to 1% MeOH in $CH_2Cl_2$ to 3% MeOH in $CH_2Cl_2$ to 5% MeOH in $CH_2Cl_2$ to 8% MeOH in $CH_2Cl_2$) provided 5-(3-bromo-3-hydroxy-butyl)-pyrrolidin-2-one (6.76 g). $^1$H NMR ($CDCl_3$) δ7.36–7.09 (m, 4H), 6.27 (d, 1H), 3.78 (m, 1H), 3.63 (m, 1H), 2.75 (m, 1H), 2.62 (m, 1H), 2.32–2.18 (m, 3H), 1.88 (m, 1H), 1.73–1.42 (m, 5H); MS 312.2, 314.1 (M+).

Step C: 5-[3-Bromo-3-(tert-butyl-dimethyl-silanyloxy)-butyl]-pyrrolidin-2-one

To a solution of 5-(3-bromo-3-hydroxy-butyl)-pyrrolidin-2-one (6.76 g, 21.6 mmol) in DMF (86 mL) was added tert-butyldimethylsilyl chloride (3.59 g, 23.8 mmol) followed by imidazole (2.95 g, 43.3 mmol) and DMAP (264 mg, 2.16 mmol). The reaction was stirred for 24 h and was quenched with saturated aqueous ammonium chloride. The aqueous solution was washed with EtOAc (3×) and the combined organic extracts were dried ($MgSO_4$), filtered, and concentrated. Purification by medium pressure chromatography using a solvent gradient ($CH_2Cl_2$ to 1% MeOH in $CH_2Cl_2$ to 3% MeOH in $CH_2Cl_2$ to 5% MeOH in $CH_2Cl_2$ to 8% MeOH in $CH_2Cl_2$) provided 5-[3-bromo-3-(tert-butyl-dimethyl-silanyloxy)-butyl]-pyrrolidin-2-one (7.45 g). $^1$H NMR ($CDCl_3$) δ7.30 (m, 2H), 7.12 (m, 1H), 7.04 (m, 1H), 5.71 (m, 1H), 3.81 (m, 1), 3.56 (m, 1H), 2.66 (m, 2H), 2.32–2.17 (m, 3H), 1.70–1.35 (m, 5H), 0.82 (s, 9H), −0.06 (d, 3H), −0.24 (d, 3H); MS 426.2, 428.2 (M+).

Step D: 5-[4-Biphenyl-3-yl-3-(tert-butyl-dimethyl-silanyloxy-butyl]-pyrrolidin-2-one To a solution of 5-[3-bromo-3-(tert-butyl-dimethyl-silanyloxy)-butyl]-pyrrolidin-2-one (750 mg, 1.76 mmol) in DME (15 mL) was added phenylboronic acid (236 mg, 1.93 mmol). Palladium acetate (26.8 mg, 0.088 mmol) and tri-o-tolylphosphine (39.5 mg, 0.176 mmol) were added followed by a solution of $Na_2CO_3$ (37.3 mg, 3.52 mmol) in water (1.8 mL). The reaction was heated at reflux for 24 h. The reaction was cooled and the volatiles were removed in vacuo. The residue was diluted with brine and EtOAc. The aqueous solution was washed with EtOAc (3×) and the combined organic extracts were dried ($MgSO_4$), filtered, and concentrated. Purification by medium pressure chromatography eluting with a solvent gradient (1:1 hexanes:EtOAc to EtOAc to 1% MeOH in $CH_2Cl_2$ to 3% MeOH in $CH_2Cl_2$ to 5% MeOH in $CH_2Cl_2$) provided 5-[4-biphenyl-3-yl-3-(tert-butyl-dimethyl-silanyloxy)-butyl ]-pyrrolidin-2-one (717.3 mg). $^1$H NMR ($CDCl_3$) δ7.57 (m, 2H), 7.43 (m, 2H), 7.33 (m, 3H), 7.11 (m, 2H), 5.78 (m, 1H), 3.91 (m, 1H), 3.59 (m, 1H), 2.76 (m, 2H), 2.27 (m, 3H), 1.73–1.38 (m, 5H), 0.83 (s, 9H), −0.03 (d, 3H), −0.16 (d, 3H); MS 424.3 (M+1).

Preparation 9

5-[3-(tert-Butyl-dimethyl-silanyloxy)-4-(3-fluoro-phenyl)-butyl]-pyrrolidin-2-one Step A: 5-[4-(3-Fluoro-phenyl)-3-oxo-butyl]-pyrrolidin-2-one Following the procedure described for Preparation 8, Step A, tetrahydro-pyrrolizine-3,5-dione (2 g, 14 mmol) was reacted with 3-fluorobenzylmagnesium chloride (0.25M in $Et_2O$, 62 mL, 15.5 mmol) over 2.5 h. Purification by medium pressure chromatography using a solvent gradient (1:1 hexanes:EtOAc to 2:1 EtOAc:hexanes to EtOAc to 2% MeOH in $CH_2Cl_2$ to 10% MeOH in $CH_2Cl_2$) provided 5-[4-(3-fluoro-phenyl)-3-oxo-butyl]-pyrrolidin-2-one (2.1730 g). $^1$H NMR ($CDCl_3$) δ7.32–7.27 (m, 1H), 7.00–6.90 (m, 3H), 6.12 (bs, 1H) 3.69 (s, 2H), 3.59 (m, 1H), 2.52 (t, 2H), 2.30 (m, 2H), 2.19 (m, 1H), 1.75 (m, 2H), 1.65 (m, 1H).

Step B: 5-[4-(3-Fluoro-phenyl)-3-hydroxy-butyl]-pyrrolidin-2-one

Following the procedure described for Preparation 8, Step B, 5-[4-(3-fluoro-phenyl)-3-oxo-butyl]-pyrrolidin-2-one (2.17 g, 8.71 mmol) was reduced with NaBH$_4$ (165 mg, 4.35 mmol). Purification by medium pressure chromatography using a solvent gradient (1:1 hexanes:EtOAc to EtOAc to 1% MeOH in CH$_2$Cl$_2$ to 3% MeOH in CH$_2$Cl$_2$ to 6% MeOH in CH$_2$Cl$_2$) provided 5-[4-(3-fluoro-phenyl)-3-hydroxy-butyl]-pyrrolidin-2-one (2.23 g). $^1$H NMR (CDCl$_3$) δ7.27 (m, 1H), 6.94 (m, 3H), 6.38 (m, 1H), 3.82 (m, 1H), 3.66 (m, 1H), 2.79 (m, 1H), 2.67 (m, 1H), 2.33–2.21 (m, 3H), 1.92 (d, J=4.15 Hz, 1H), 1.75–1.40 (m, 5H); MS 252.2 (M+1).

Step C: 5-[3-(tert-Bul-dimethyl-silanyloxy)-4-(3-fluoro-phenyl)-butyl]-pyrrolidin-2-one Following the procedure described for Preparation 8, Step C, 5-[4-(3-fluoro-phenyl)-3-hydroxy-butyl]-pyrrolidin-2-one (2.23 g, 8.87 mmol) was reacted with tert-butyldimethylsilyl chloride (1.47 g, 9.76 mmol). Purification by medium pressure chromatography using a solvent gradient (1:1 hexanes:EtOAc to EtOAc to 1% MeOH in CH$_2$Cl$_2$ to 2% MeOH in CH$_2$Cl$_2$ to 4% MeOH in CH$_2$Cl$_2$) provided 5-[3-(tert-butyl-dimethyl-silanyloxy)-4-(3-fluoro-phenyl)-butyl]-pyrrolidin-2-one (2.84 g). $^1$H NMR (CDCl$_3$) δ7.23 (m, 1H), 6.88 (m, 3H), 5.75 (m, 1H), 3.85 (m, 1H), 3.57 (m, 1H), 2.71 (m, 2H), 2.30 (m, 2H), 2.25 (m, 1H), 1.70–1.38 (m, 5H), 0.84 (s, 9H), 0 (s, 3H). –0.2 (s, 3H).

Preparation 10

5-[3-(tert-Butyl-dimethyl-silanyloxy)-4-(4-fluoro-phenyl)-butyl]-pyrrolidin-2-one Step A: 5-[4-(4-Fluoro-phenyl)-3-oxo-butyl]-pyrrolidin-2-one Following the procedure described for Preparation 8, Step A, tetrahydro-pyrrolizine-3,5-dione (1.41 g, 10.1 mmol) was reacted with 4-fluorobenzylmagnesium chloride (0.25M in Et$_2$O, 50 mL, 12.5 mmol) over 5 h. Purification by medium pressure chromatography (2% MeOH in CH$_2$Cl$_2$) provided 5-[4-(4-fluoro-phenyl)-3-oxo-butyl]-pyrrolidin-2-one (2.64 g). $^1$H (CDCl$_3$) δ7.18 (m, 2H), 7.03 (m, 2H), 6.34 (m, 1H), 3.70 (s, 2H), 3.62 (m, 1H), 2.54 (t, 2H), 2.34–2.15 (m, 3H), 1.82–1.61 (m, 3H).

Step B: 5-[4-(4-Fluoro-phenyl)-3-hydroxy-butyl]-pyrrolidin-2-one

Following the procedure described for Preparation 8, Step B, 5-[4-(4-fluoro-phenyl)-3-oxo-butyl]-pyrrolidin-2-one (2.64 g, mmol) was reduced with NaBH$_4$ (400 mg, mmol) at room temperature for 1 h. Additional NaBH$_4$ (150 mg) was added and the reaction was stirred for 20 h. Purification by medium pressure chromatography using a solvent gradient (CH$_2$Cl$_2$ to 2% MeOH in CH$_2$Cl$_2$ to 4% MeOH in CH$_2$Cl$_2$) provided 5-[4-(4-fluoro-phenyl)-3-hydroxy-butyl]-pyrrolidin-2-one (2.01 g). $^1$H NMR (CDCl$_3$) δ7.14 (m, 2H), 6.98 (m, 2H), 6.78 (m, 1H), 3.76 (m, 1H), 3.65 (m, 1H), 2.76 (m, 1H), 2.64 (m, 1H), 2.32–2.18 (m, 4H), 1.72–1.47 (m, 5H).

Step C: 5-[3-(tert-Butyl-dimethyl-silanyloxy)-4-(4-fluoro-phenyl)-butyl]-pyrrolidin-2-one Following the procedure described for Preparation 8, Step C, 5-[4-(4-fluoro-phenyl)-3-hydroxy-butyl]-pyrrolidin-2-one (1.95 g, 7.79 mmol) was reacted with tert-butyldimethylsilyl chloride (1.47 g, 9.76 mmol). Purification by medium pressure chromatography (1% MeOH in CH$_2$Cl$_2$) provided 5-[3-(tert-butyl-dimethyl-silanyloxy)-4-(4-fluoro-phenyl)-butyl]-pyrrolidin-2-one. $^1$H NMR (CDCl$_3$) δ7.12 (m, 2H), 6.97 (m, 2H), 5.75 (m, 1H), 3.83 (m, 1H), 3.60 (m, 1H), 2.71 (m, 2H), 2.36–2.24 (m, 3H), 1.70–1.38 (m, 5H), 0.84 (s, 9H), –0.05 (d, 3H), –0.2 (d, 3H).

Preparation 11

[2-Oxo-3-(3-phenoxy-phenyl)-propyl]-phosphonic acid dimethyl ester

Substituting the appropriate starting materials, the title compound of Preparation 11 was made in an analogous manner to that described for the compound of Preparation 5.

What is claimed is:

1. 7-{2S-[3R-hydroxy-4-(3-phenoxy-phenyl)-butyl]-5-oxo-pyrrolidin-1-yl}-heptanoic acid; or a pharmaceutically acceptable salt thereof.

2. The compound of claim 1 which is 7-{2S-[3R-hydroxy-4-(3-phenoxy-phenyl)-butyl]-5-oxo-pyrrolidin-1-yl}-heptanoic acid.

3. A method for treating a condition which presents with low bone mass in a mammal comprising administering to said mammal a compound selected from 7-{2S-[3R-hydroxy-4-(3-phenoxy-phenyl)-butyl]-5-oxo-pyrrolidin-1-yl}-heptanoic acid; 7-(2S-(3R-hydroxy-4-(3-trifluoromethyl-phenyl)-butyl)-5-oxo-pyrrolidin-1-yl)-heptanoic acid; 7-{2S-[4-(3-chloro-phenyl)-3R-hydroxy-butyl]-5-oxo-pyrrolidin-1-yl}-heptanoic acid; 5S-[4-(3-chloro-phenyl)-3R-hydroxy-butyl]-1-[6-(2H-tetrazol-5-yl)-hexyl]-pyrrolidin-2-one; and 5S-(3R-hydroxy-4-(3-trifluoromethyl-phenyl)-butyl)-1-(6-(2H-tetrazol-5-yl)-hexyl)-pyrrolidin-2-one, or a pharmaceutically acceptable salt thereof.

4. A method of claim 3 wherein said condition is osteoporosis, frailty, an osteoporotic fracture, a bone defect, childhood idiopathic bone loss, alveolar bone loss, mandibular bone loss, bone fracture, osteotomy, bone loss associated with periodontitis, or prosthetic ingrowth.

5. A method of claim 4 wherein said compound is administered systemically.

6. A method of claim 4 wherein said compound is administered locally.

7. A method of claim 4 wherein said condition is frailty.

8. A method of claim 4 wherein said condition is osteoporosis.

9. A method of claim 4 wherein said condition is bone fracture or osteoporotic fracture.

10. A method of claim 4 wherein said condition is a bone defect.

11. A method of claim 4 wherein said condition is childhood idiopathic bone loss.

12. A method of claim 4 wherein said condition is alveolar bone loss.

13. A method of claim 4 wherein said condition is mandibular bone loss.

14. A method of claim 4 wherein said condition is bone loss associated with periodontitis.

15. A method of claim 4 wherein said condition is osteotomy or prosthetic ingrowth.

* * * * *